(12) United States Patent
Koyama et al.

(10) Patent No.: US 6,482,806 B1
(45) Date of Patent: *Nov. 19, 2002

(54) PRODUCT OF HEAT TREATMENT OF URONIC ACID, FOOD, DRINK, OR DRUG INCLUDING THE PRODUCT

(75) Inventors: Nobuto Koyama, Otsu (JP); Hiroaki Sagawa, Otsu (JP); Eiji Kobayashi, Otsu (JP); Tatsuji Enoki, Otsu (JP); Hua-Kang Wu, Otsu (JP); Eiji Nishiyama, Otsu (JP); Suzu Deguchi, Otsu (JP); Katsushige Ikai, Otsu (JP); Hiromu Ohnogi, Otsu (JP); Motoko Ueda, Otsu (JP); Akihiro Kondo, Otsu (JP); Ikunoshin Kato, Otsu (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/125,397
(22) PCT Filed: Feb. 25, 1997
(86) PCT No.: PCT/JP97/00527
§ 371 (c)(1),
(2), (4) Date: Aug. 18, 1998
(87) PCT Pub. No.: WO97/33593
PCT Pub. Date: Sep. 18, 1997

(30) Foreign Application Priority Data

| Mar. 15, 1996 | (JP) | 8-085972 |
| Jun. 14, 1996 | (JP) | 8-174411 |
| Aug. 16, 1996 | (JP) | 8-233719 |
| Sep. 27, 1996 | (JP) | 8-275231 |
| Nov. 22, 1996 | (JP) | 8-325900 |

(51) Int. Cl.[7] ............ A61K 31/727; A61K 31/728; A61K 31/732; A61K 31/734; A61K 31/715; A61P 35/00

(52) U.S. Cl. ............ 514/54; 514/56; 514/62
(58) Field of Search ............ 424/440; 514/54, 514/56, 62, 557, 451

(56) References Cited

U.S. PATENT DOCUMENTS 5,476,842 A * 12/1995 Rubin et al. ............ 514/25
6,207,652 B1 * 3/2001 Sakai et al.

FOREIGN PATENT DOCUMENTS

| JP | 52-105199 | 9/1977 |
| JP | 57-163478 | 10/1982 |
| JP | 60-23319 | 2/1985 |

(List continued on next page.)

OTHER PUBLICATIONS

Brennan, Carbohydrate–Based Drug Delivery Polysaccharide transport mechanism and cell–surface engineering open new routes, Chemical and Engineering News, pp. 50–53, May 1997.*

Primary Examiner—Edward J. Webman
(74) Attorney, Agent, or Firm—Wenderoth, Lind & Ponack, L.L.P.

(57) ABSTRACT

A product obtained by heating at least one substance selected from the following (a), (b) and (c).
  (a) uronic acid or uronic acid derivative;
  (b) a saccharide compound containing uronic acid or a saccharide compound containing uronic acid derivative; and
  (c) a substance containing a saccharide compound containing uronic acid or a substance containing a saccharide compound containing uronic acid derivative;
and food, beverage or a pharmaceutical agent which is characterized in containing the above-mentioned heat-treated product.

8 Claims, 15 Drawing Sheets

FOREIGN PATENT DOCUMENTS

| | | |
|---|---|---|
| JP | 62-29947 | 2/1987 |
| JP | 63-226292 | 9/1988 |
| JP | 4-18401 | 1/1992 |
| JP | 4-36228 | 2/1992 |
| JP | 4-335839 | 11/1992 |
| JP | 7-506493 | 7/1995 |
| JP | 7-215990 | 8/1995 |
| JP | 7-228544 | 8/1995 |

* cited by examiner

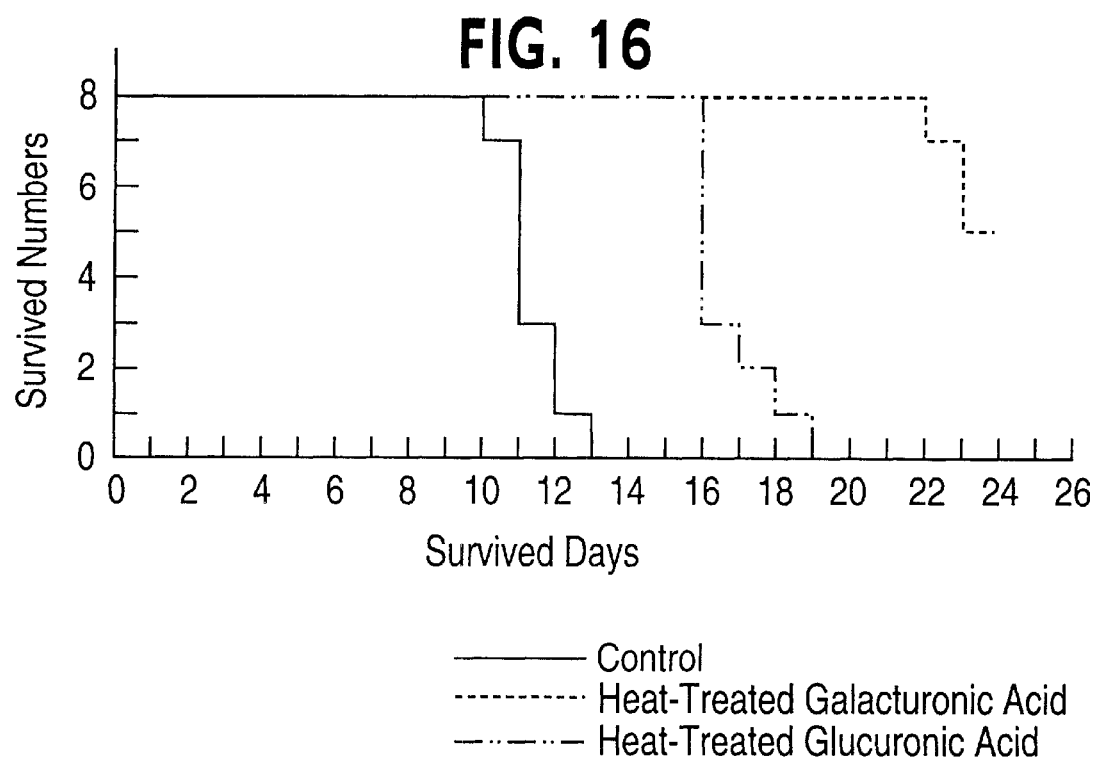

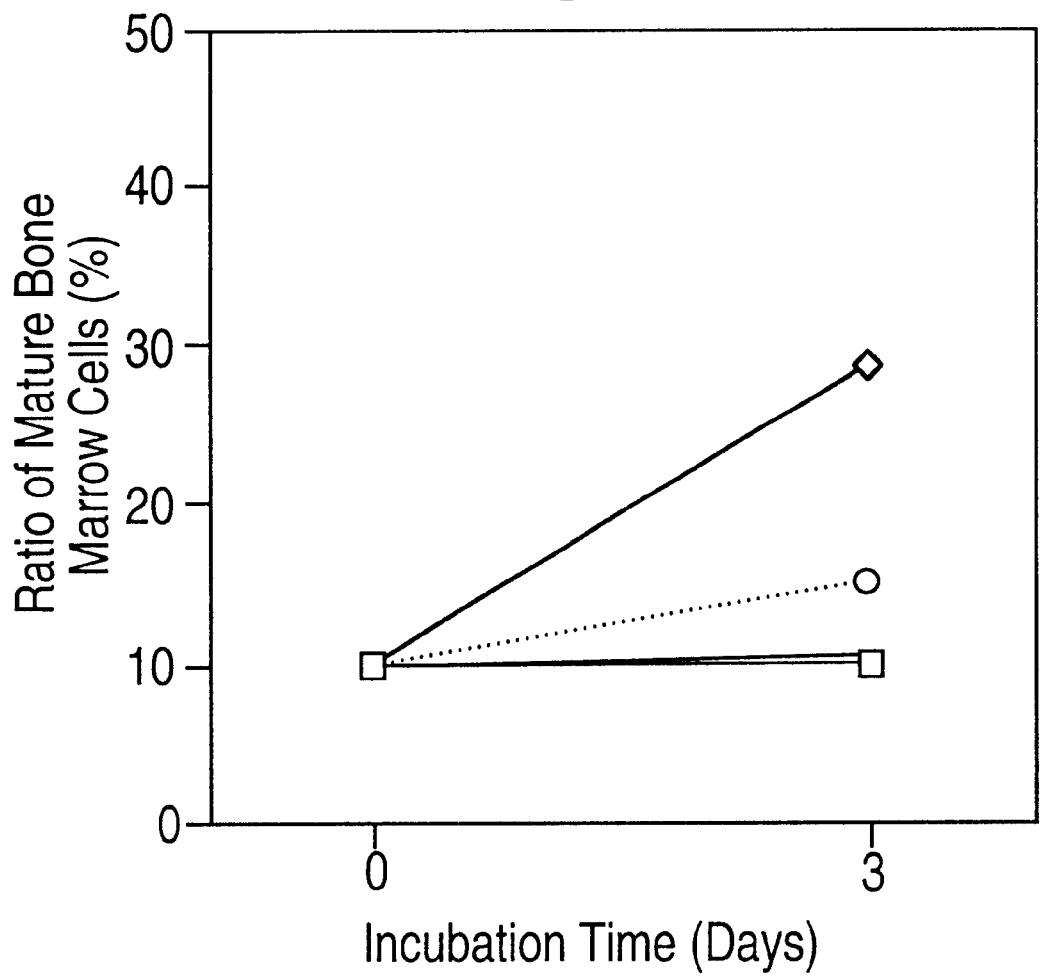

PRODUCT OF HEAT TREATMENT OF URONIC ACID, FOOD, DRINK, OR DRUG INCLUDING THE PRODUCT

BACKGROUND OF THE INVENTION

1. Field of the Invention

An object of the present invention is to develop a product containing a highly safe and physiologically active substance having an anticancer action, an apoptosis-inducing action, and the like, and to offer a functional food or beverage exhibiting a high physiological effect containing said product. The present invention also offers antibacterial agents, dentifrices, antiseptic agents, apoptosis inducers, anticancer agents and antiulcer agents containing said product as an effective component. The present invention further offers a method for inducing apoptosis where said method is useful, for example, in elucidating the mechanism of apoptosis and in screening the apoptosis inhibitors. The present invention still further offers a method for the manufacture of a product containing the physiologically active substance of the present invention.

2. Description of the Related Art

In recent years, a phenomenon called "apoptosis" which is a self-destructive cell death or a suicidal cell death has attracted attentions regarding the death of cell tissues.

Unlike a necrosis which is a pathological cell death, an apoptosis is considered to be the death which is inherently programmed in genes of the cells themselves. Thus, it is believed that some external or internal factors trigger the activation of genes which program the apoptosis whereby a programmed death gene protein is biosynthesized based upon the genes and the cells themselves are decomposed by the resulting programmed death gene protein whereby the death is resulted.

If such an apoptosis can be expressed in a desired tissue or cell, it will be quite meaningful because unnecessary or pathogenic cells such as cancer cells can be eliminated from the living body in a natural manner.

SUMMARY OF THE INVENTION

An object of the present invention is to develop a product containing a highly safe and physiologically active substance having an anticancer action, an apoptosis-inducing action, and the like whereby a method for the manufacture of said product and also food or beverage containing said product are offered. Another object of the present invention is to offer pharmaceuticals such as antibacterial agents and apoptosis inducers containing said compound and to offer a method of inducing an apoptosis using said product as an effective component.

An outline of the present invention will be as follows. Thus, the first aspect of the present invention is a product obtained by heating at least one substance selected from the following (a), (b) and (c).

(a) uronic acid or uronic acid derivative;
(b) a saccharide compound containing uronic acid or a saccharide compound containing uronic acid derivative; and
(c) a substance containing a saccharide compound containing uronic acid or a substance containing a saccharide compound containing uronic acid derivative.

The second aspect of the present invention is a method for the manufacture of a heat-treated product, characterized in that, said method includes a step of heating at least one substance selected from the following (a), (b) and (c).

(a) uronic acid or uronic acid derivative;
(b) a saccharide compound containing uronic acid or a saccharide compound containing uronic acid derivative; and
(c) a substance containing a saccharide compound containing uronic acid or a substance containing a saccharide compound containing uronic acid derivative.

The present inventors have found that a heat-treated product (hereinafter, said product will be referred to as a "heat-treated product of the present invention") of at least one substance selected from uronic acid, uronic acid derivative, a saccharide compound containing uronic acid, a saccharide compound containing uronic acid derivative, a substance containing a saccharide compound containing uronic acid and a substance containing a saccharide compound containing uronic acid derivative has a potent anticancer action, apoptosis-inducing action, antibacterial action and antiulcer action whereby the present invention has been achieved.

BRIEF DESCRIPTION OF THE DRAWINGS

FIG. 16 shows an anticancer action of a heat-treated product of uronic acids to a leukemia cell line; and FIG. 17 shows a differentiation-inducing action of a heat-treated product of uronic acid.

DESCRIPTION OF THE PREFERRED EMBODIMENTS

Figure 1:
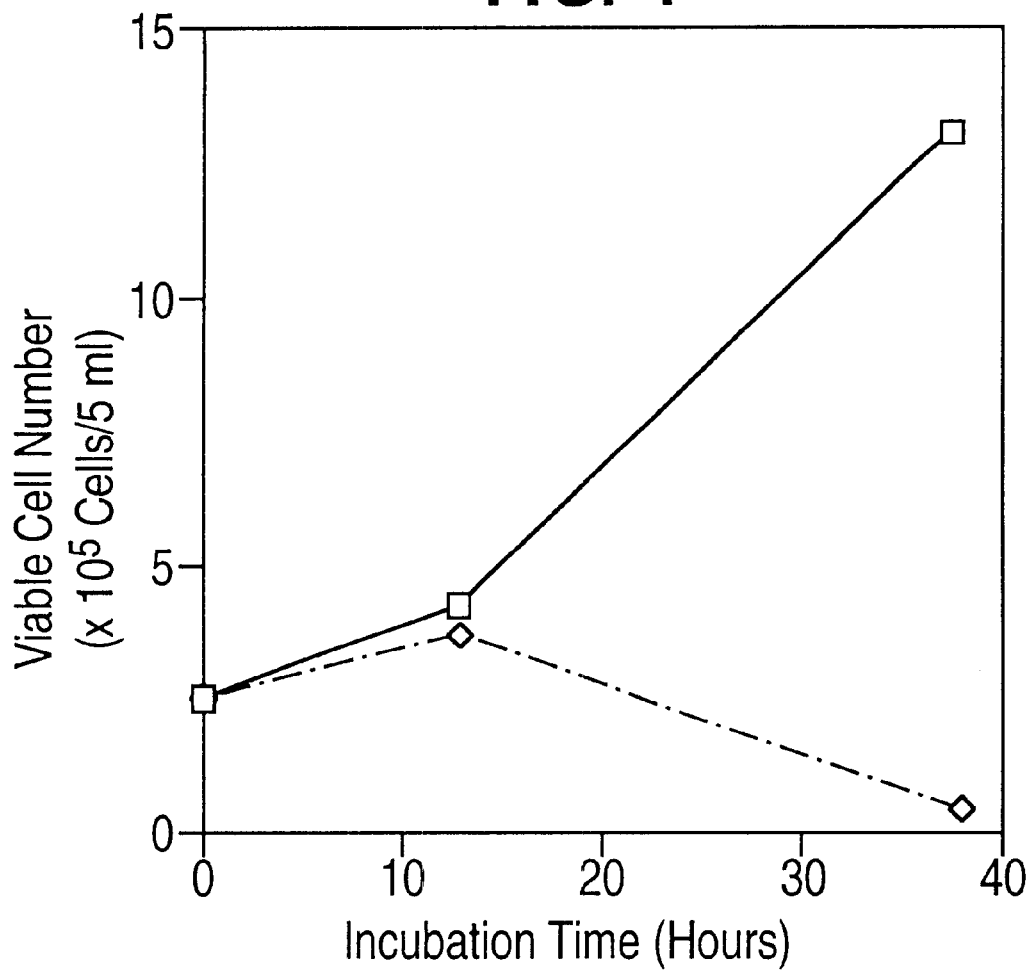
FIG. 1 shows an action of a heat-treated product of pectin to cancer cells.

The present invention will be illustrated in a specific manner as hereinafter.

In the present invention, there is no particular limitation for uronic acid, uronic acid derivative, a saccharide compound containing uronic acid, a saccharide compound containing uronic acid derivative, a substance containing a saccharide compound containing uronic acid and a substance containing a saccharide compound containing uronic acid derivative provided that the product obtained by heating them exhibits anticancer action, apoptosis-inducing actions, and the like, and that anticancer substance and/or apoptosis-inducing substance are/is produced in said heat-treated product.

Uronic acid is sometimes called glycuronic acid and is a general name for hydroxyaldehyde carboxylic acids in which an aldehyde group on aldose remains as it is while only a primary alcohol group at another end is oxidized to a carboxyl group. It is present in nature as a constituting component for various polysaccharides of animals and plants. Examples of the polysaccharides containing uronic acids are pectin, pectic acid, alginic acid, hyaluronic acid, heparin, fucoidan, chondroitin sulfate, dermatan sulfate, and the like, and they have been known to exhibit various physiological functions.

There is no particular limitation for the uronic acid used in the present invention. Thus, examples of the uronic acid are galacturonic acid, glucuronic acid, guluronic acid, mannuronic acid and iduronic acid while examples of the uronic acid derivative are lactones, esters, amides, salts, and the like, of the above-mentioned ones and any substance which produces anticancer substance and/or apoptosis-inducing substance by heat treatment is covered by the derivative of the present invention. Examples of the uronic acid lactone are glucurono-6,3-lactone (hereinafter, abbreviated as glucuronolactone), mannurono-6,3-lactone and idurono-6,3-lactone. Examples of the uronic acid ester are methyl, ethyl, propylene glycol and carboxymethyl uronates which can be manufactured from uronic acid. Uronic acid amide can be manufactured by amidation of uronic acid. Salts of them can be manufactured by common methods.

The saccharide compound containing uronic acid or uronic acid derivative of the present invention means a saccharide compound containing uronic acid and/or uronic acid derivative and there is no particular limitation therefor. Thus it covers, for example, pectin, pectic acid, alginic acid, hyaluronic acid, heparin, fucoidan, chondroitin sulfate, chondroitin and dermatan sulfate including decomposed products, derivatives of the decomposed products and salts of the decomposed products thereof which are chemically, enzymatically or physically-treated products thereof.

In the above-mentioned chemical treatment, the starting saccharide compound is, for example, treated at room temperature to 200° C. for several seconds to several hours or, preferably, at 50–130° C. for several seconds to an hour (in the case of pectin, treated for example at pH 6.8, 95° C. for several minutes to several tens minutes) whereupon a beta-elimination takes place to give a saccharide compound having unsaturated uronic acid and/or unsaturated uronic acid ester in which an absorbance at around 235 nm is increased. The saccharide compound of the present invention covers a saccharide compound containing unsaturated uronic acid and/or unsaturated uronic acid ester at a non-reducing end prepared by a beta-elimination of a polysaccharide compound containing uronic acid and/or uronic acid ester.

An example of the above-mentioned enzymatic treatment is a known decomposition method in which the starting saccharide compound containing uronic acid and/or uronic acid ester is decomposed by a hydrolase for the saccharide containing uronic acid and/or uronic acid ester. Another example is a known decomposition method in which the saccharide containing uronic acid and/or uronic acid ester is decomposed by a lyase for the saccharide containing uronic acid and/or uronic acid ester. For example, in the case of pectin or pectic acid, a decomposition is conducted by a known pectin lyase (EC 4.2.2.10), pectic acid lyase (EC 4.2.2.2) or exopolygalacturonic acid lyase (EC 4.2.2.9) to give a saccharide compound having 4-deoxy-L-threo-hex-4-enopyranosyl uronate or methyl ester thereof at a non-reducing end. In the case of hyaluronic acid, a hyaluronate lyase (EC 4.2.2.1) is used while, in the case of alginic acid, an alginate lyase (EC 4.2.2.3) is used. The enzymatically decomposed products having 4-deoxy-L-threo-hex-4-enopyranosyl uronate or methyl ester thereof at the non-reducing end prepared as such are covered by the saccharide compound of the present invention as well.

Examples of the above-mentioned physical treatment are the treatment of the starting saccharide compound with near infrared ray, infrared ray, microwave, ultrasonic wave, and the like. Thus, for example, pectin and/or pectic acid are/is placed in a neutral (in terms of pH) or an alkaline solution and subjected to an ultrasonic wave for applying a vibrational energy at an appropriate temperature of not lower than room temperature under an appropriate reductive operation in the presence of, for example, ascorbic acid for not shorter than one second or, preferably, from five seconds to one hour. Besides the ultrasonic wave, it is also effective to irradiate with microwave, near infrared ray, infrared ray, and the like, or a combination thereof The irradiation may be conducted either continuously or intermittently.

In addition, in the present invention, a substance which contains the above-mentioned saccharide compound containing uronic acid and/or its derivative such as fruit, rind of a fruit, strained lees of a fruit, vegetable, strained lees of a vegetable, sea algae, and the like, may be used either as it is or after being dried and crushed. Further, a liquid of the saccharide compound containing uronic acid and/or its derivative obtained by extracting the above-mentioned substance which contains a saccharide compound containing uronic acid and/or its derivative, or a purified substance obtained from said extracted liquid may be used as well. Preparation of such an extracted liquid of the saccharide compound containing uronic acid and/or its derivative and purification from the extracted liquid may be conducted by known methods and there is no particular limitation therefor.

Examples of the substance which contains the saccharide compound containing uronic acid or uronic acid ester are as follows. Thus, fruits, vegetables, leaves, seeds, and the like of dicotyledons such as apple, citrus fruits (e.g., mandarin orange and lemon), banana, nappa cabbage, cabbage, lettuce, perilla, pumpkin, celery, burdock, echalote, broccoli, green pepper, spinach, carrot, leaves of carrot, leaves of daikon (Japanese radish), tea leaves, sesame, beans, potato, and the like; cereals of monocotyledons such as wheat and rice; algae such as brown algae (e.g., sea tangle and wakame seaweed), red algae, green algae and unicellular green algae; microorganisms such as Basidiomycetes (e.g., Lyophyllum ulmarium, Lyophyllum decastes, Pholiota nameko, Cortinellus shiitake, Flammulina verutipes, Agaricus ostreatus and Pasalliota campestris), Ascomycetes (e.g., Cordyceps militaris and other Cordyceps sp.), yeasts, filamentous fungi (e.g., Aspergillus sp.) and bacteria (e.g., Bacillus natto and lactic acid bacteria); and animals such as vertebrates and invertebrates. In the present invention, a substance which contains a saccharide compound containing uronic acid and/or uronic acid derivatives derived from the above-mentioned plants, microorganisms or animals may be used.

The polysaccharides which are saccharide compounds containing uronic acid and/or uronic acid derivatives can be manufactured by known chemical, enzymatic or physical methods. In the case of pectin for example, a high-molecular polysaccharide extracted from, for example, rind of citrus fruits or apple may be used. Materials for the manufacture of pectin on an industrial scale are fruits and, in addition to strained lees (mostly comprising endocarp) after preparing juice of citrus fruits such as lemon and lime, the strained lees after preparation of apple juice is used as well. Such strained lees mostly contain insoluble protopectin and it is solubilized (extracted) during the course of manufacture to prepare pectin. Solubilization can be conducted by extracting with acidic warm to hot water and, when the conditions such as temperature, pH and time are properly controlled depending upon the type of the starting material, it is possible to manufacture pectin having predetermined molecular weight and degree of esterification in a high yield. The extract is purified by means of centrifugation or filtration and concentrated and alcohol is added thereto whereupon pectin can be precipitated and recovered. The recovered precipitate is dried and crushed to prepare a dry pectin.

The main structure of pectin is a partially methylated galacturonic acid polymer. The carboxyl group is either methylated, left as a free acid or made into a salt such as ammonium salt, potassium salt or sodium salt. Depending upon the degree of methylation (DM; ratio of methoxyl groups to total carboxyl groups), pectin is classified into an HM pectin having a high DM and an LM pectin having a low DM ["Handbook of Materials for Developing New Food Products" edited by Satoshi Yoshizumi, et al., published by K. K. Korin, pages 114–119 (1991)] and, in the present invention, pectin which is commercially available as a food additive ["Handbook of Natural Products" edited by Akio Toyama, et al., published by Shokuhin To Kagakusha, 12th Edition, page 138 (1993)], commercially available HM pectin and LM pectin, and the like, [refer to the above-mentioned "Handbook of Materials for Developing New Food Products"] may be used.

Decomposed product of a saccharide compound containing uronic acid and/or uronic acid derivative may be manufactured by known chemical, enzymatic or physical treating methods. Uronic acid, uronic acid derivatives, oligosaccharides, and the like which are manufactured by synthetic means are also covered by the present invention.

The heat-treated product which is used in the present invention may be manufactured from a material selected from (a) uronic acid or uronic acid derivative; (b) a saccharide compound containing uronic acid or a saccharide compound containing uronic acid derivative; and (c) a substance containing a saccharide compound containing uronic acid or a substance containing a saccharide compound containing uronic acid derivative.

With regard to a method for the heating treatment in the manufacture of the heat-treated product of the present invention, uronic acid, uronic acid derivative, a saccharide compound containing uronic acid, saccharide compound containing uronic acid derivative, a substance containing a saccharide compound containing uronic acid and/or a substance containing a saccharide compound containing uronic acid derivative are/is heated, for example, at 60–350° C. for several seconds to several days or, preferably, at 80–150° C. for several minutes to several days. In the case of pectin, a heat-treated product having a physiological activity such as anticancer action or apoptosis-inducing action can be prepared by heating the pectin, for example, at 80–150° C. for several minutes to several days while, in the case of uronic acids, uronic acid lactones and uronic acid esters, desired heat-treated product can be prepared by heating them at 60–150° C. for several minutes to several days.

Although there is no particular limitation for the pH during the heating treatment, it is preferred to conduct the heating under neutral to acidic conditions and, depending upon the material used, the pH during the heating may be adjusted. Usually, however, production of physiologically active substances such as anticancer substance, apoptosis-inducing substance, and the like is promoted by heating under an acidic condition.

There is no particular limitation for the concentration of the material upon heating provided that the concentration is within such a range that the physiologically active substances such as anticancer substance, apoptosis-inducing substance, and the like, can be produced by the heating treatment. Thus, the concentration may be decided by taking workability, yield, and the like into consideration.

The heating treatment in the present invention may be either wet heating or dry heating. In the case of a wet heating, any of wet heating methods such as heating with steam, heating with steam under high pressure, heating under high pressure, and the like, may be used while, in the case of a dry heating, any of dry heating methods such as a direct heating using dry and hot air and an indirect heating from a heat source through a partition may be used. Examples of the direct heating are a dry heating by an air stream and a dry heating by means of spraying while those of the indirect heating are a dry heating by means of a drum, and the like. In addition, the material for the heating treatment of the present invention may be treated by any of common heating methods such as boiling, toasting, roasting, decocting, steaming, frizzling, flying, and the like.

The heat-treated product of the present invention is a heat-treated product obtained by the above-mentioned heating methods and a fraction containing a physiologically active substance in said heat-treated product.

The heat-treated product of the present invention contains two or more substances which showapoptosis-inducing action, anticancer action, antibacterial action, antiviral action, and the like. In addition, reductons having antoxidative action are also produced during the heating treatment of the present invention. Therefore, when the conditions for the heating treatment are changed according to the object, it is possible to prepare the heat-treated product of the present invention having a desired substandce, The heat-treated produt of the present invention can be fractionated using its physiological activity as an index. For example, the molecular weight fractionation of the heat-treated product is conducted by a known method such as gel filtration or fractionation using a molecular weight fractionating membrane to prepare each molecular weight fraction whereupon the geattreated product of the present invention having a high activity can be prepared. Further, a desired fraction can be also prepared by solvent extraction, fractional distillation and various chromatographic methods using ion exchange resin, and the like.

Examples of gel filtration are that, when Cellulofine GCL-300 is used, it is possible to prepare any of the molecular weight fractions such as those where the molecular weight (MW) is MW>25,000; 25,000≧MW>10,000; 10,000≧MW>5,000; and 5,000≧MW while, when Cellulofine GCL-25 is used, it is possible, for example, to fractionate a fraction of 5,000≧MW into any of the molecular weight fractions such as 5,000 2≧MW >3,000; 3,000≧MW>2,000; 2,000≧MW>1,000; 1,000≧MW>500; and 500≧MW.

When an ultrafiltration membrane is used, the molecular weight fractionation can be conducted on an industrialscale. For example, when FE10-FUSO382 (manufactured by Daicel) is used, it is possible to prepare a fraction having a molecular weight of 30,000 and less while, when FE-FUS-T653 (manufactured by the same company) is used, it is possible to prepare a fraction having a molecular weight of 6,000 and less. Further, the use of a nanofilter membrane is able to give a fraction having a molecular weight of 500 or less. When the above-mentioned gel filtration and molecular weight fractionation are combined, any of the molecular weight fractions may be prepared.

In the heat-treated product of the present invention, the fraction having a molecular weight of 30,000 or less has strong anticancer and apoptosis-inducing activities and, particularly, the fraction having a molecular weight of 10,000 or less or, preferably, that of 500 or less has strong anticancer, apoptosis-inducing and antibacterial activities. Thus, depending upon the object, the molecular weight fractionated fraction of the heat-treated product of the present invention can be used as an effective component of the heat-treated product of the present invention.

The heat-treated product of the present invention has an inhibiting activity to the growth of cancer cells. The action mechanism of the heat-treated product of the present invention does not limit the present invention at all and, for example, an apoptosis-inducing action to cancer cells is included in the coverage of the present invention.

The heat-treated product of the present invention has a growth-inhibiting action and apoptosis-inducing action to cancer cells such as human promyelocytic leukemia cells (HL-60), human acute lymphoblastic leukemia cells (MOLT-3), pulmonary cancer cells (A-549), SV40 transformed lung cells (WI-38VA13), hepatic cancer cells (Hep G2), colon cancer cells (HCT 116), human colon cancer cells (SW 480), human colon cancer cells (WiDr), gastric cancer cells (AGS) and myeloma cells and the amount of the anticancer substance in the heat-treated product of the present invention can be expressed in terms of an anticancer activity unit.

The anticancer activity unit used in the present specification is defined as follows. Thus, the heat-treated solution of the present invention is used as a sample, 0.5 ml of its diluted solution is added to 4.5 ml of an RPMI 1640 medium containing 10% of fetal calf serum and $2.5 \times 10^5$ human promyelocytic leukemia cells (HL-60) (ATCC CCL-240), incubated in the presence of 5% carbon dioxide gas at 37° C. for 24 hours, numbers of the living cells are counted and the anticancer activity per ml of the medium when the cell survival rate is 50% of the control is defined as-one unit. Thus, when the anticancer activity per ml of the medium is calculated as one unit, then 1 ml of the sample has 10 units of anticancer activity.

Survival rate (R) of the cell in terms of % is calculated by the following formula.

$$R = Vs/(Vs+Ds) \times 100 + Dc/(Vc+Dc) \times 100$$

In the formula, Vs and Ds are numbers of viable cells and dead cells, respectively, in the section where the sample has been added; and Vc and Dc are numbers of viable and dead cells, respectively, in the section where water has been added.

The heat-treated product of the present invention is a substance derived from natural food and no toxicity is observed upon oral and parenteral administrations to mice.

There is no particular limitation for the food and the beverage of the present invention and their examples are processed agricultural and forest products, processed livestock products, processed marine products, and the like, such as confectionery, bread, noodles, beverages (both alcoholic and nonalcoholic), seasonings, brewing products (soybean paste, soybean sauce and vinegar), alcoholic drinks and spices manufactured from the raw materials such as cereals, potato, starch, sweeteners, fat/oil, seeds, beans, fish/shellfish, meat of animals, birds and whales, eggs, milks, vegetables, fruits, mushrooms, algae, and the like.

There is no particular limitation for the methods of manufacturing the food or the beverage of the present invention and their examples are cooking, processing and commonly-used manufacturing methods for food and beverages. Any method may be used so far as the manufactured food or beverage contains the heat-treated product of the present invention.

In the cause of cooking and processing, any method may be used so far as the product after cooking or processing contains the heat-treated product of the present invention having anticancer action, apoptosis-inducing action, and the like.

Thus, the heat-treated product of the present invention may be added before, during or after cooking or processing. Alternatively, the cooked or processed product of a material thereof may be added to the heat-treated product of the present invention having anticancer action, apoptosis-inducing action, and the like, whereby said heat-treated product is diluted.

Then, in the manufacture of food or beverage, a heating treatment may be conducted in any desired step so that the heat-treated product of the present invention having anticancer action, apoptosis-inducing action, and the like, is made contained therein; the heat-treated product of the present invention having anticancer action, apoptosis-inducing action, and the like, may be added thereto; or food, beverage or a material thereof may be added to the heat-treated product of the present invention having anticancer action, apoptosis-inducing action, and the like, so that said heat-treated product is diluted. Addition may be conducted at a time or dividedly in several times. Therefore, it is possible to easily manufacture a novel food or beverage having anticancer action, apoptosis-inducing action, and the like. The present invention also covers the food or beverage wherein uronic acid, uronic acid lactone, uronic acid ester, a saccharide compound containing uronic acid and/or uronic acid ester or a substance containing such a saccharide compound is made contained during its manufacture so that the food or beverage is made to consist of its heat-treated product having anticancer action, apoptosis-inducing action, and the like, produced during the manufacture. When the product is manufactured by any of those steps, the food or beverage containing the heat-treated product of the present invention having anticancer action, apoptosis-inducing action, and the like, and those prepared by adding and/or diluting the heat-treated product of the present invention are defined as the food or the beverage of the present invention.

There is no particular limitation for the content of the heat-treated product of the present invention having anticancer action, apoptosis-inducing action, antibacterial action, and the like but may be suitably chosen in view of its organoleptic property and physiological activity. For example, however, the content of the heat-treated product in 100 parts of food is 0.001 part or more in terms of the heat-treated product of a solid state and, in view of organoleptic property as food, physiological activity such as anticancer action, apoptosis-inducing action and antibacterial action and the cost, the content is preferably 0.005–10 parts or, more preferably, 0.0 1–1part.

There is no particular limitation for the amount of the heat-treated product of the present invention having anticancer action, apoptosis-inducing action, antibacterial action, and the like in the beverage and may be suitably selected in terms of its organoleptic property and physiological activity. For example, however; the content of the heat-treated product in 100 parts of the beverage is 0.001 part or more in terms of the heat-treated product of a solid state and, in view of taste as beverage, physiological activity such as anticancer action, apoptosis-inducing action and antibacterial action and the cost, the content is preferably 0.005–10 parts or, more preferably, 0.01–1 part. Incidentally, the part means that by weight in the present specification.

Although the amount of the heat-treated product in the food of the present invention having an anticancer action may be suitably selected in view of the anticancer activity, the amount per 100 g of the food is 0.1 unit or more in terms of the anticancer activity unit, preferably 10 units or more or, more preferably, 100 units or more.

Although there is no particular limitation for the amount of the heat-treated product having an anticancer action of the present invention but the amount may be suitably selected in view of the anticancer activity, the amount per 100 g of the beverage is 0.1 unit or more in terms of the anticancer activity unit, preferably 10 units or more or, more preferably, 100 units or more.

There is no particular limitation for the shape of the food or the beverage of the present invention so far as the heat-treated product of the present invention having anticancer action, apoptosis-inducing action, antibacterial action, and the like, is contained therein, added thereto and/or diluted therein and the shapes which can be orally taken such as tablets, granules, capsules, gel, sol, and the like, are adopted.

The food or beverage of the present invention contains the heat-treated product of the present invention having a physiological activity in a large amount and is a healthy or a functional food or beverage exhibiting carcinogenesis preventing effect, cancer suppressing effect, antiulcer effect, liver function improving effect, constipation preventing effect, preventing effect for cold by influenza virus and preventing effect for Alzheimer's disease due to various physiological activities of said heat-treated product such as antibacterial action, apoptosis-inducing action, anticancer action, antiviral action, antiulcer action, antiangiogenic action, liver function improving action, dietary fiber action, action of removing unnecessary metals such as iron and heavy metals, and the like. The food or beverage is particularly useful for keeping stomach and intestine healthy. In addition, it is a food or beverage having a very good preservability because of its antibacterial action.

The heat-treated product of the present invention may be used as an antiseptic agent for improving the preservability of food or beverage. In addition, the heat-treated product of the present invention may be used in a method for making food or beverage antiseptic by adding it to food or beverage.

The heat-treated product of the present invention having an antibacterial action can be easily prepared by heating uronic acid, uronic acid lactone, uronic acid ester, a saccharide compound containing uronic acid and/or a saccharide compound containing uronic acid ester, and the like, and the use of the antibacterial agent containing the heat-treated product of the present invention derived from natural food to food or beverage is quite excellent in terms of safety.

The form of the antibacterial agent containing the heat-treated product of the present invention upon its addition to food or beverage may be any of liquid, paste, powder, flakes, granules, and the like. When an easy operation or the use by mixing with other additives are taken into consideration, it is preferred to make the agent powdery, flaky or granular by drying. With regard to the method for drying, commonly-used one such as spray-drying, drum drying, shelf drying, vacuum drying, freeze-drying, and the like, may be used.

The antibacterial agent and antiseptic agent of the present invention may be manufactured by any of methods which are known to the persons skilled in the art. Upon the manufacture, known additives which are permissible for preparing a formulation such as bulking agents, stabilizers, disintegrating agents, binders, auxiliary solubilizers, and the like, may be appropriately added. Other antibacterial substances such as ethanol, glycine, sodium acetate, ascorbic acid, glycerol fatty acid esters, salt, EDTA, and the like, may be jointly used therewith.

Amount of the heat-treated product of the present invention to be added to food or beverage may vary depending upon the type of the food or beverage and the amount meeting with the object may be added.

One method of using the antibacterial agent of the present invention is that where the agent is added to food or to beverage by an appropriate method. There is no particular limitation for a method of addition but that will do ultimately if the heat-treated product of the present invention is contained in food or beverage by any means. Accordingly, in the use of the antibacterial agent of the present invention, the term "addition" covers all methods whereby the heat-treated product of the present invention is made contained in the food or beverage. Although the common method is to add it during the manufacturing steps of the food or beverage, a method where the food is dipped in a solution containing the heat-treated product of the present invention may be used as well. It is also possible to conduct a method of adding it to the food together with a method of dipping the food in the solution. Examples of the food which is suitable for a dipping method are the food which does not lose its shape even in water such as fish or livestock meat paste (e.g., kamaboko [boiled fish paste] and Vienna sausage), noodles (e.g., boiled noodle) and frozen product of fish, shellfish and shrimp before freezing.

When the antibacterial agent of the present invention is used as an antiseptic agent, preservability of food or beverage can be further improved. In the case of frozen food and frozen desert, growth of contaminated microorganisms in the processing step before freezing can be suppressed whereby a very favorable result in terms of hygiene can be obtained. The antibacterial agent of the present invention is effective to both gram-positive and gram-negative bacteria and is very effective, for example, to drug-resistant bacteria such as methicillin-resistant Staphylococcus aureus and bacteria which cause food poisoning such as Salmonella, enterotoxin-producing Staphylococcus aureus, Bacillus cereus of a vomiting type, Bacillus cereus of a diarrhea type and enterorrhagial Escherichia coli O-157. Said agent is effective to microorganisms such as yeasts and fungi as well. The antiseptic agent containing the heat-treated product of the present invention is particularly and highly useful as a natural preventive agent for food poisoning and as a sterilizing agent. Incidentally, sterilization of clothing, bed sheet, and the like, can be conducted using the antibacterial agent of the present invention and, when the antibacterial agent of the present invention is sprinkled or when wiping-off with the antibacterial agent of the present invention is conducted, it is possible to sterilize (both to remove and to kill the bacteria) the object to be sterilized.

The antibacterial agent of the present invention shows an antibacterial activity to bacteria for dental caries, and those for periodontal disease and an intraoral preparations containing the antibacterial agent of the present invention can be offered. The form of the intraoral preparation may be a known one such as liquid or paste. An example of the intraoral preparation is a dentifrice. The dentifrice may be in a known form such as liquid, paste or powder. There is no particular limitation for the amount of the heat-treated product of the present invention in the dentifrice and, if an effective concentration to the bacteria for dental caries and for periodontal disease is contained therein, that will be enough. Known additives such as moisturizing agents, surface-active agents, binders, perfumes, sweetening agents, and the like, may be added to the dentifrice. As mentioned already, heat-treated product of the substances which contain a saccharide compound containing uronic acid or uronic acid ester such as pectin-containing substance (e.g. vegetables and fruits) may be used as well and an intraoral preparation containing a heat-treated product of pectin-containing vegetable such as dentifrice may be included in the coverage of the present invention.

To prepare the apoptosis inducer of the present invention, the heat-treated product of the present invention having an apoptosis-inducing ability is employed as the active ingredient and compounded with known pharmaceutical carriers to give a pharmaceutical preparation. Usually, the heat-treated product of the present invention is compounded with pharmaceutically acceptable liquid or solid carriers followed, if necessary, by adding solvents, dispersing agents, emulsifiers, buffers, stabilizers, bulking agents, binders, disintegrating agents, lubricants and the like thereto whereupon solid preparations such as tablets, granules, diluted powders, powders, capsules, and the like, or liquid preparations such as solutions, suspensions, emulsions, and the like, are prepared. The resulting preparation may be processed into a dry one which can be then liquefied prior to use by adding an appropriate carrier thereto.

The apoptosis inducer of the present invention can be administered either orally or parenterally by, for example, injection or intravenous drip infusion.

The pharmaceutical carriers may be appropriately selected depending upon the administration route and dosage form as mentioned above. Starch, lactose, sucrose, mannitol, carboxymethylcellulose, corn starch, inorganic salts and the like may be used in the case of the oral preparations. In preparing the oral preparations, it is also possible to add binders, disintegrating agents, surface-active agents, lubricants, fluidity improving agents, corrigents, coloring agents, perfumes and the like thereto.

On the other hand, in the case of parenteral preparations, the heat-treated product having an apoptosis inducing activity which is an active ingredient of the present invention is dissolved or suspended by a common manner in a diluent such as distilled water for injection, physiological saline solution, aqueous solution of glucose, plant oil for injection, sesame oil, peanut oil, soybean oil, corn oil, propylene glycol or polyethylene glycol followed, if necessary, by adding bactericides, stabilizers, isotonic agent, analgesic agents, and the like thereto whereupon the desired parenteral preparation is obtained.

The apoptosis inducer of the present invention is administered via an appropriate administration route depending upon the dosage form. There is no particular limitation for the method of administration as well and any of internal and external route and a route by injection may be selected therefor. Injections may be administered, for example, by intravenous, intramuscular, subcutaneous and intradermal routes while preparations for external use include suppositories.

The dose of the apoptosis inducers of the present invention is not particularly specified but may be appropriately determined depending upon the dosage form, administration method, purpose of the use and the age, body weight, conditions, and the like, of the patient to whom the inducer is administered. Usually, however, the dose of the heat-treated product of the present invention contained in the preparation for an adult is 20–2,000 mg/kg per day. As a matter of course, the dose may vary depending upon various factors and, therefore, less dose than the above-mentioned one may be sufficient in some cases while, in other cases, more dose than the above may be necessary. The agent of the present invention may be administered orally as it is and, further, the agent may be taken daily after adding to common food and/or beverage as well.

An anticancer agent can be manufactured when the heat-treated product of the present invention having an anticancer action is used as an active ingredient and is made into a pharmaceutical preparation together with known pharmaceutical carriers. The anticancer agent may be manufactured in accordance with the method mentioned above. Usually, the heat-treated product of the present invention is compounded with pharmaceutically acceptable liquid or solid carriers followed, if necessary, by adding solvents, dispersing agents, emulsifiers, buffers, stabilizers, bulking agents, binders, disintegrating agents, lubricants, and the like, to give solid preparations such as tablets, granules, diluted powders, powders, capsules, and the like, or liquid preparations such as solutions, suspensions, emulsions, and the like. Alternatively, it may be processed into a dry preparation which can be liquefied by adding an appropriate carrier thereto before actual use.

The anticancer agent of the present invention may be administered either orally or parenterally by, for example, means of injection or intravenous drip infusion.

The pharmaceutical carriers may be appropriately selected depending upon the above-mentioned administration route and dosage form and may be used in the same manner as in the case of the apoptosis inducer mentioned already.

The anticancer agent is administered by an appropriate administration route depending upon the dosage form. There is no particular limitation for the administration method and, for example, administration by internal or external route or by injection may be conducted. Injections may be administered, for example, by intravenous, intramuscular, subcutaneous and intradermal routes while preparations for external use include suppositories.

The dose of the anticancer agent of the present invention is not particularly specified but may be appropriately determined depending upon the dosage form, administration method, purpose of the use and the age, body weight, conditions, and the like, of the patient to whom the agent is administered. Usually, however, the dose of the heat-treated product of the present invention contained in the preparation for adults is 20–2,000 mg/kg per day. As a matter of course, the dose may vary depending upon various factors and, therefore, less dose than the above-mentioned one may be sufficient in some cases while, in other cases, more dose than the above may be necessary. The agent of the present invention may be administered orally as it is and, further, the agent may be taken daily after adding to common food and/or beverage as well.

The heat-treated product of the present invention has an anticancer action and, at low concentrations, it has an ability of inducing a differentiation of cancer cells whereby the heat-treated product of the present invention is also useful as a differentiation-inducing agent (decarcinogenic agent). The differentiation inducer for cancer cells containing the heat-treated product of the present invention as an active ingredient can be made into preparations by the same manner in the case of the anticancer agent mentioned above and can be administered by the same method as that in the case of the anticancer agent.

The dose of the agent as a differentiation inducer for cancer cells is not particularly specified but may be appropriately determined depending upon the dosage form, administration method, purpose of the use and the age, body weight, conditions, and the like, of the patient to whom the inducer is administered. Usually, however, the dose of the heat-treated product of the present invention contained in the preparation for an adult is 0.2–500 mg/kg per day. As a matter of course, the dose may vary depending upon various factors and, therefore, less dose than the above-mentioned one may be sufficient in some cases while, in other cases, more dose than the above may be necessary. The agent of the present invention may be administered orally as it is and, further, the agent may be taken daily after adding to common food and/or beverage as well.

The heat-treated product of the present invention has an antiviral effect and an action of improving the hepatic function. Accordingly, antiviral agent and a hepatic function improving agent containing the heat-treated product of the present invention as an active ingredient can be prepared by the same manner as in the case of the above-mentioned anticancer agent and can be administered by the same manner as in the case of the anticancer agent.

The dose as the antiviral agent and the hepatic function improving agent is not particularly specified but may be appropriately determined depending upon the dosage form, administration method, purpose of the use and the age, body weight, conditions, and the like, of the patient to whom the agent is administered. Usually, however, the dose of the heat-treated product of the present invention contained in the preparation for adults is 0.2–2,000 mg/kg per day. As a matter of course, the dose may vary depending upon various factors and, therefore, less dose than the above-mentioned one may be sufficient in some cases while, in other cases, more dose than the above may be necessary. The agent of the present invention may be administered orally as it is and, further, the agent may be taken daily after adding to common food and/or beverage as well. When the preparation containing the heat-treated product of the present invention is administered, viral diseases such as common cold caused by influenza virus can be prevented and treated and, in addition, hepatic function disorder can be improved as well whereby GOT and GPT values become normal.

The heat-treated product of the present invention has an action of inducing a heat shock protein of, for example, 70-k daltons and exhibits an antiviral action to RNA viruses and DNA viruses such as hepatitis virus, AIDS virus, influenza virus, herpes virus, and the like. It shows a bioprotective action such as an antiinflammatory action.

An antiulcer agent can be prepared by using the heat-treated product of the present invention having an antiulcer action as the active ingredient together with known pharmaceutical carriers followed by processing into a-pharmaceutical preparation. The antiulcer agent can be prepared in accordance with the method described above. Usually, the heat-treated product of the present invention is compounded with pharmaceutically acceptable liquid or solid carriers followed, if necessary, by adding solvents, dispersing agents, emulsifiers, buffers, stabilizers, bulking agents, binders, disintegrating agents, lubricants, and the like thereto whereby solid preparations such as tablets, granules, diluted powders, powders, capsules, and the like, or a liquid preparations such as solutions, suspensions, emulsions, and the like, are prepared. It is also possible to prepare a dry product which can be made into liquid by addition of an appropriate carrier before use.

The antiulcer agent may be administered by an oral route or by a parenteral route as injections or intravenous drip infusion.

The pharmaceutical carrier may be selected depending upon the above-mentioned administration manner and dosage form and may be used by the same manner as in the case of the above-mentioned apoptosis inducer.

The antiulcer agent may be administered via an appropriate administration route depending upon the dosage form. The administration method is not particularly limited too and administration by internal or external route or by injection may be conducted. Injections may be administered, for example, by intravenous, intramuscular, subcutaneous or intradermal route. Preparations for external use include suppositories.

The dose as the antiulcer agent is not particularly specified but may be appropriately determined depending upon the dosage form, administration method, purpose of the use and the age, body weight, conditions, and the like, of the patient to whom the agent is administered. Usually, however, the dose of the heat-treated product of the present invention contained in the preparation for an adult is 20–2,000 mg/kg per day. As a matter of course, the dose may vary depending upon various factors and, therefore, less dose than the above-mentioned one may be sufficient in some cases while, in other cases, more dose than the above may be necessary. The agent of the present invention may be administered orally as it is and, further, the agent may be taken daily after adding to common food and/or beverage as well.

The present invention offers food or beverage which has a physiological activity such as anticancer action and apoptosis-inducing action, induces anticancer action or apoptosis in ill cells in the patients suffering from cancer or viral diseases and is effective for prevention and therapy of said disease. Especially in the case of cancer of digestive organs such as cancer of stomach and colon, it is possible to inhibit the growth of cancer cells or to result in apoptosis in cancer cells by giving the heat-treated product of the present invention by oral route as food or beverage and, therefore, the food or beverage where the heat-treated product of the present invention is contained therein, added thereto and/or diluted therein has an excellent effect for therapy and prevention of cancers of digestive organs.

In addition, the heat-treated product of the present invention has antiviral and antibacterial actions. Therefore, it is useful as antiviral agent, antibacterial agent, intraoral agent (such as dentifrice) and antiseptic agent for food or beverage and, due to its antiulcer action, it is also useful as antiulcer agent and a preventive agent for ulcer. Further due to its action for improving the hepatic function, it is useful as a hepatic function improving agent too.

It is now possible in accordance with the present invention that the food or beverage of the present invention contains a large amount of the heat-treated product of the present invention having a physiological activity. The food or beverage of the present invention is a healthy or functional food or beverage exhibiting a maintenance action of homeostasis of living body such as carcinogenesis preventing effect, anticancer effect, antibacterial effect, antiviral effect, antiulcer effect, constipation preventing effect, hepatic function improving effect, preventing effect for Alzheimer disease, apoptosis-inducing effect, and the like, due to various physiological activities of said heat-treated product such as apoptosis-inducing action, antibacterial action, anticancer action, antiviral action, antiangiogenic action inhibitory, action for abnormally proliferating cells, antiulcer action, hepatic function improving action, dietary fiber action, action of removing unnecessary metals such as iron and heavy metals, and the like. Thus, in accordance with the present invention, food or beverage containing functional substances which is useful for keeping stomach and intestine healthy. When the heat-treated product of the present invention, especially a fraction having a molecular weight of 500 or less, is added, the antibacterial activity of food and beverage can be easily made strong and, therefore, the heat-treated product of the present invention is quite useful as an antiseptic agent for food and beverage as well. Due to its various physiological functions, when the heat-treated product of the present invention (particularly a fraction having a molecular weight of 10,000 or less or, preferably, that having a molecular weight of 500 or less) is used in food or beverage, it is now possible to easily give various physiological functions to food or beverage. Thus, the heat-treated product is quite useful, for example, as an antibacterial additive to food or beverage and also as an antiseptic agent for food or beverage.

The present invention further offers an apoptosis inducer and an anticancer agent which are useful for prevention and therapy of patients suffering from cancer and viral diseases by inhibiting the proliferation of pathogenic cells and by inducing apoptosis to pathogenic cells due to its anticancer and apoptosis-inducing actions. Especially in the case of cancer of digestive organs such as cancer of stomach and colon, it is possible to inhibit the growth of cancer cells or to result in apoptosis in cancer cells by administering the heat-treated product of the present invention by oral route as food or beverage and, therefore, the food or beverage where the heat-treated product of the present invention is contained therein, added thereto and/or diluted therein has an excellent effect for therapy and prevention of cancers of digestive organs. The present invention furthermore offers an antiulcer agent having an antiulcer action which is useful for prevention and therapy of ulcer for the patients suffering from said disease. In the case of ulcer of digestive organs, the heat-treated product of the present invention achieves an antiulcerative action by taking it orally as food or beverage and, therefore, the food or beverage where the heat-treated product of the present invention is added thereto and/or diluted therein has an excellent effect for therapy and prevention of ulcers of digestive organs. The pharmaceutical agent of the present invention can be supplied in low cost and in large quantities using edible fruit rind, edible algae, and the like as a starting material and another advantage is that it has a high safety because it is derived from food. Moreover, a simple method for inducing apoptosis can be offered by the present invention and, when the method of the present invention is used, it is now possible to study for clarifying the mechanism of apoptosis and to develop inhibitors to an apoptosis induction.

EXAMPLES

The present invention will be further illustrated by way of the following examples although the present invention is never limited by and to those examples. Incidentally, the term % used in the examples means that by weight.

Example 1

Pectin which was manufactured from apple (manufactured by Wako Pure Chemicals) (500 mg) was suspended in 50 ml of 50 mM HEPES buffer (pH: 7.0) containing 120 mM of NaCl and autoclaved at 121° C. for 20 minutes to prepare a heat-treated pectin solution.

Human promyelocytic leukemia cells HL-60 (ATCC CRL-1964) were incubated in an RPMI 1640 medium (manufactured by Nissui) containing 10% of fetal calf serum (manufactured by Gibco) treated at 56° C. for 30 minutes and then suspended in an ASF 104 medium (manufactured by Ajinomoto) to make the cell concentration $5 \times 10^5$ cells/9 ml.

To this suspension was added 1 ml of the heat-treated pectin solution and the mixture was incubated at 37° C. for 16 hours in the presence of 5% of carbon dioxide. For the sake of confirmation, the same incubation as above was conducted except that 0.1 ml of aqueous solution (0.1 mg/ml) of actinomycin D (manufactured by Sigma) which was known as an apoptosis-inducing reagent and 0.9 ml of a physiological saline solution were used instead of the above-mentioned pectin solution.

The incubated cells were observed under an optical microscope whereupon condensation of nuclei, contraction of cells and production of apoptotic body were confirmed in both of the heat-treated pectin solution and the actinomycin D-added incubated cells. Incidentally, in the control where the cells to which 1 ml of physiological saline solution was added were incubated, such phenomena were not observed.

From those results, it was found that the heat-treated pectin solution induced apoptosis in HL-60 cells.

Example 2

Commercially available pectin manufactured from apple was dissolved in a 50 mM HEPES buffer (pH: 7.0) containing 120 mM of NaCl so as to make the final concentration of the pectin 10 mg/ml and then the solution was adjusted to pH 7.0 with 1N NaOH. This was heated at 121° C. for 30 minutes and its ultraviolet absorption spectrum was measured whereupon the absorbance at around 235 nm of the heat-treated product increased as compared with that before heating.

This sample was adjusted to pH 7.0 with 1N NaOH and the apoptosis-inducing activity was measured by a method mentioned in Example 1. In this and all of the succeeding examples, however, there were some exceptions that an RPMI 1640 medium containing 10% of fetal bovine serum was used instead of an ASF 104 medium, that HL-60 (ATCC CCL-240) was used as the cells and that, upon measurement of the apoptosis-inducing activity, each of the samples was adjusted to pH 7.0 with 1N NaOH whereby the apoptosis-inducing activity was measured. To the cell suspension was added twice as much by volume of 0.4% aqueous solution of trypan blue and an observation was conducted under an optical microscope whereby trypan blue was excreted and colorless cells and blue-colored cells were counted as viable and dead cells, respectively.

As a result thereof, the heat-treated pectin product showed a significant apoptosis-inducing activity to HL-60 cells.

Commercially available pectin from lemon was dissolved in 50 mM HEPES buffer (pH: 7.0) containing 120 mM of NaCl to make the concentration of the pectin 10 mg/ml whereupon the pH was 5.0. This was heated at 121° C. for 30 minutes and an ultraviolet absorption spectrum was measured whereupon the absorbance at around 235 nm increased in the heat-treated product.

This sample was adjusted to pH 7.0 with 1N NaOH and, when the apoptosis-inducing activity to HL-60 cells was measured by the above-mentioned method, the heat-treated product was found to exhibit a significant apoptosis-inducing activity.

The results are shown in FIG. 1. Thus FIG. 1 shows a relationship between the incubation time and the viable cell number in the culture medium when a heat-treated lemon pectin solution was added to a culture medium of HL-60 cells to make the pectin concentration 1 mg/ml wherein the abscissa is the incubation time (hours) while the ordinate is the viable cell number ($\times 10^5$ cells/5 ml) in the culture medium. In FIG. 1, the open square stands for the control where no sample was added while the open rhombus stands for the case where heat-treated lemon pectin was added. Thus, the heat-treated lemon pectin showed an anticancer action.

Example 3

(1) Commercially available pectin manufactured from apple was dissolved in 50 mM HEPES buffer (pH: 7.0) containing 120 MM of NaCl to make the pectin concentration 10 mg/ml and heated at 121° C. for 20 minutes to prepare a heat-treated solution. A part of it was freeze-dried to give a heat-treated solution made into a freeze-dried state.

Then the remaining part of the heat-treated solution was dialyzed against pure water using a Seamless cellulose tubing (cutoff molecular weight: 12,000–14,000; manufactured by Sanko Junyaku) or Spectra/Por 7 dialyzing membrane (cutoff molecular weight: 1,000; manufactured by Spectrum) and each of the inner liquids after dialysis was freeze-dried and weighed whereupon, in each of the freeze-dried inner liquids, there was a loss in weight of about 10% as compared with the pectin before the heating treatment.

The freeze-dried heat-treated solution was dissolved in water while the freeze-dried inner liquid after the dialysis was dissolved in 50 mM HEPES buffer (pH: 7.0) containing 120 mM of NaCl whereupon the final concentration of each of the both solutions was made 10 mg/ml. The solution was adjusted to pH 7.0 with 1NaOH and an apoptosis-inducing activity to HL-60 cells was measured by the method as mentioned in Example 2.

The results were that the heat-treated pectin solution showed an activity while the inner liquid after the dialysis showed a decreased activity.

Figure 2:
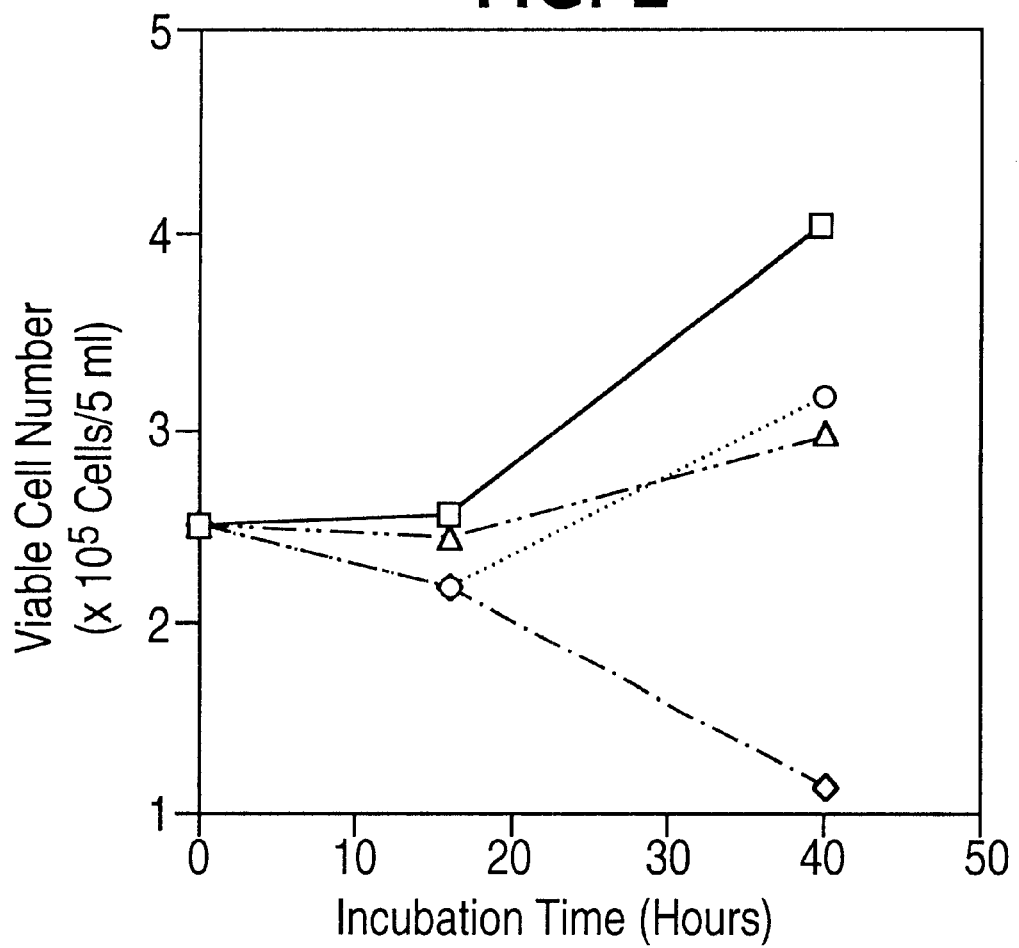
FIG. 2 shows an action to cancer cells of the samples before and after dialysis.

The results are shown in FIG. 2. Thus, FIG. 2 shows the relationship between the incubation time and the viable cell number in the culture medium when a freeze-dried heat-treated solution, a freeze-dried inner liquid after dialyzed using a cellulose membrane or a freeze-dried inner liquid after dialyzed using Spectra/Por 7 dialyzing membrane was added to a culture medium of HL-60 cells to make the concentration 1 mg/ml wherein the abscissa stands for the incubation time (hours) while the ordinate stands for the viable cell number ($\times 10^5$ cells/5 ml) in the culture medium. In FIG. 2, open square stands for the control where no sample was added; open rhombus stands for the case where the freeze-dried product of the heat-treated solution was added; open circle stands for the case where freeze-dried product of the inner liquid after the dialysis through cellulose membrane was added; and open triangle stands for the case where freeze-dried product of the inner liquid after the dialysis through the Spectra/Por 7 dialyzing membrane was used. Thus, the heat-treated solution exhibited an anticancer action.

(2) After the above-mentioned heat-treated pectin solution was adjusted to pH 7.0 with 1N NaOH and subjected to an ultrafiltration using a Centriplus 10 (fractionating molecular weight: 10,000; manufactured by Amicon) to prepare a fraction which passed through the membrane. The apoptosis-inducing activity of this fraction was measured by a method mentioned in Example 2 whereupon it had the same activity as the sample before the ultrafiltration had.

Figure 3:
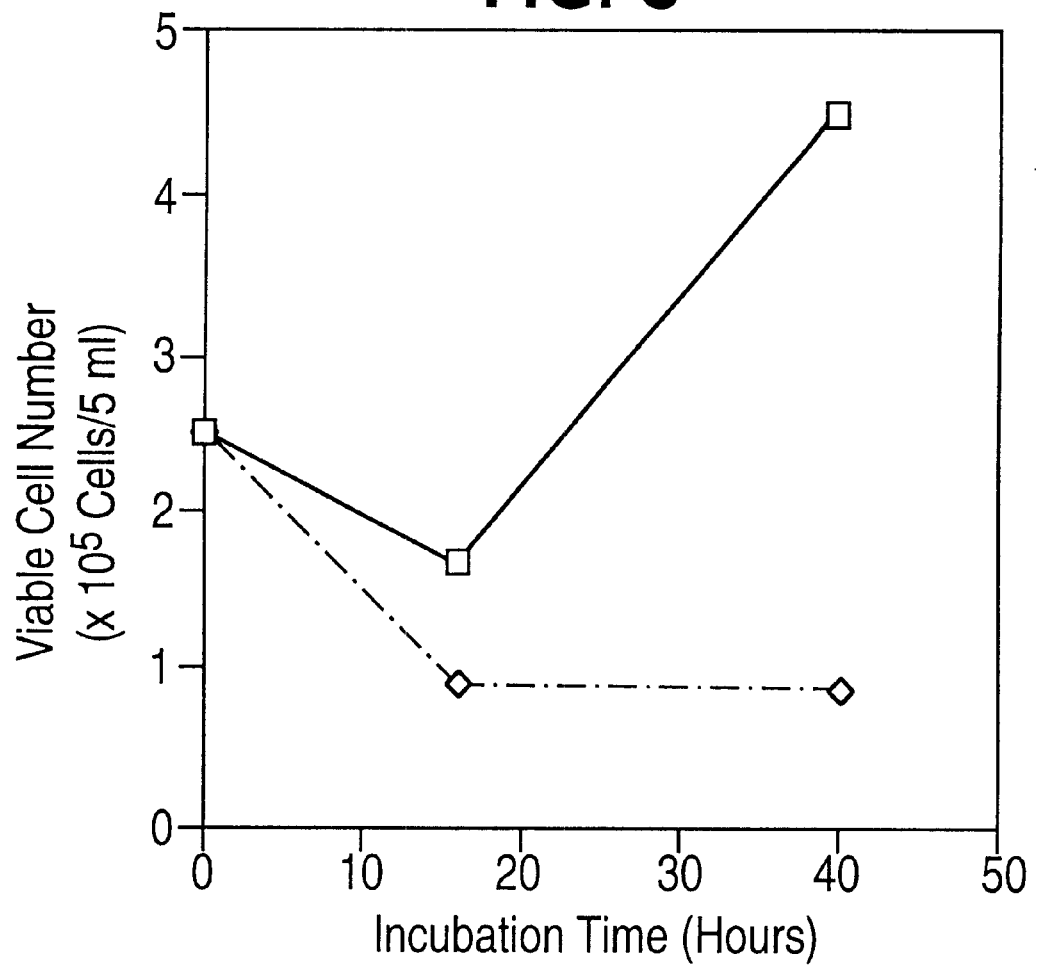
FIG. 3 shows an action to cancer cells of the filtrate obtained by ultrafiltration.

The results are shown in FIG. 3. Thus, FIG. 3 shows the relationship between the incubation time and the viable cell number in the culture medium when a fraction of the heat-treated pectin solution passing through Centriplus 10 was added to a culture medium of HL-60 cells to make the concentration 1 mg/ml wherein the abscissa stands for the incubation time (hours) while the ordinate stands for the viable cell number ($\times 10^5$ cells/5 ml) in the culture medium. In FIG. 3, open square stands for the control where no sample was added and open rhombus stands for the case where the fraction passing through the membrane was added. Thus, the heat-treated pectin solution exhibited the same result as the case of open rhombus and the heat-treated pectin solution and the fraction passing through the membrane showed an anticancer action.

Example 4

Commercially available pectin manufactured from apple was dissolved in 50 mM HEPES buffer (pH: 7.0) containing 120 mM of NaCl to make the pectin concentration 10 mg/ml and the solution was adjusted to pH 7.0 with 1N NaOH and heated at 121° C. for 30 minutes. This sample (20 ml) was applied to a column of Sephacryl S-300 Hiload 26/60 High Resolution (manufactured by Pharmacia) equilibrated with pure water and subjected to gel filtration. Pure water was used for the mobile phase at the flow rate of 1 ml/minute and detection was performed by a differential refractometer.

Each of the fraction 1 (which was eluted after 110–190 minutes from application of the sample to the column), fraction 2 (eluted after 190–270 minutes) and fraction 3 (eluted after 270–400 minutes) was concentrated by means of an evaporator. To each of the fraction were added NaCl and HEPES to make their final concentrations 120 mM and 50 mM, respectively and to make the volume 20 ml. This was adjusted to pH 7.0 with 1N NaOH.

An apoptosis-inducing activity to HL-60 cells was measured by the method of Example 2 whereupon a strong activity was found in the fraction 3 having the lowest molecular weights.

Figure 4:
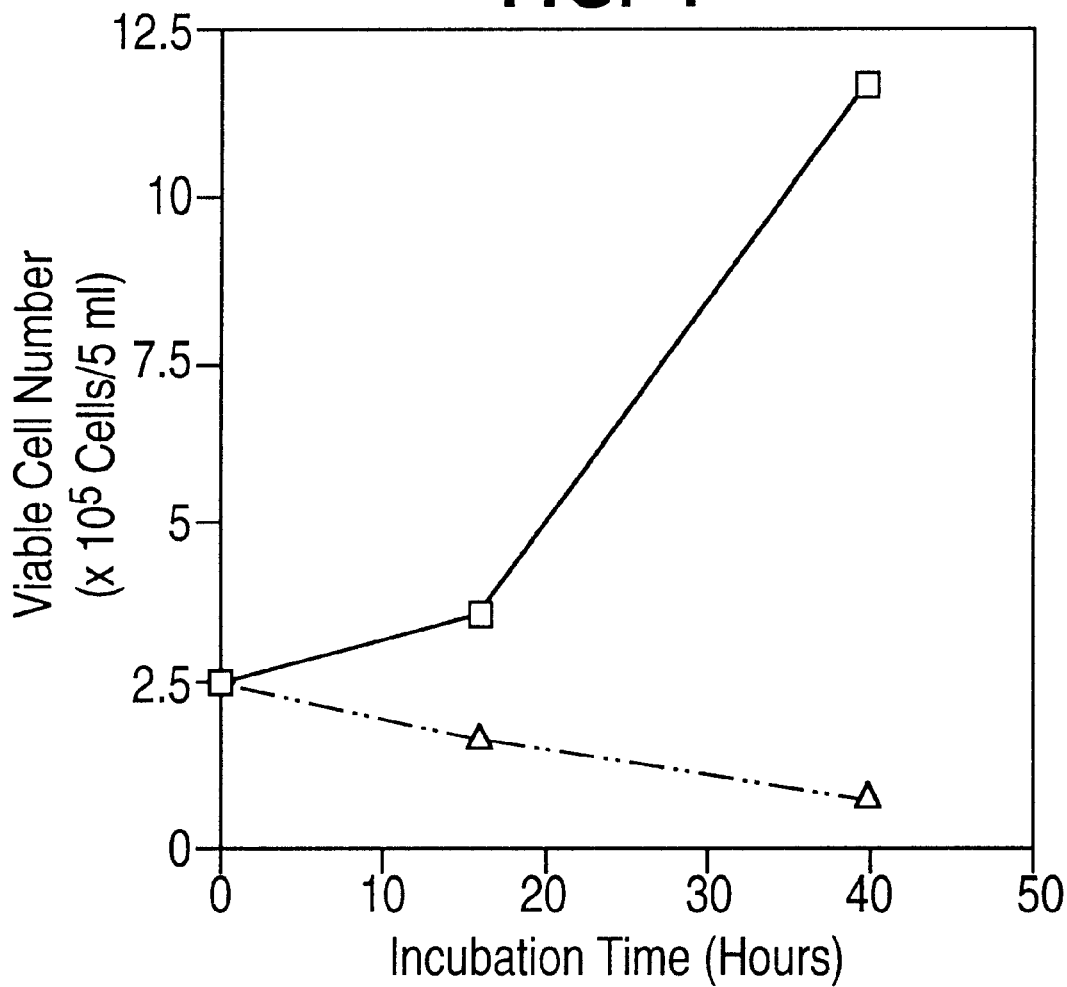
FIG. 4 shows an action to cancer cells of the fraction obtained by a gel filtration.

The results are shown in FIG. 4. Thus, FIG. 4 shows the relationship between the incubation time and the viable cell number in the culture medium when the above-mentioned fraction 3 was added to a culture medium of HL-60 cells to make the concentration 1 mg/ml wherein the abscissa stands for the incubation time (hours) while the ordinate stands for the viable cell number ($\times 10^5$ cells/5 ml) in the culture medium. In FIG. 4, open square stands for the control where no sample was added and open triangle stands for the case where the fraction 3 was added. Thus, the fraction 3 exhibited an anticancer action.

Example 5

D-α-galacturonic acid or D-glucuronic acid were dissolved in 50 mM HEPES buffer (pH: 7.0) containing 120 mM of NaCl to make the concentration of the acids 10 mg/ml. The resulting solutions were heated at 121° C. for 20 minutes and adjusted to pH 7.0 with 1N NaOH. The apoptosis-inducing activity of those samples to HL-60 cells was measured by the method of Example 2 whereupon both samples exhibited significant activity.

Figure 5:
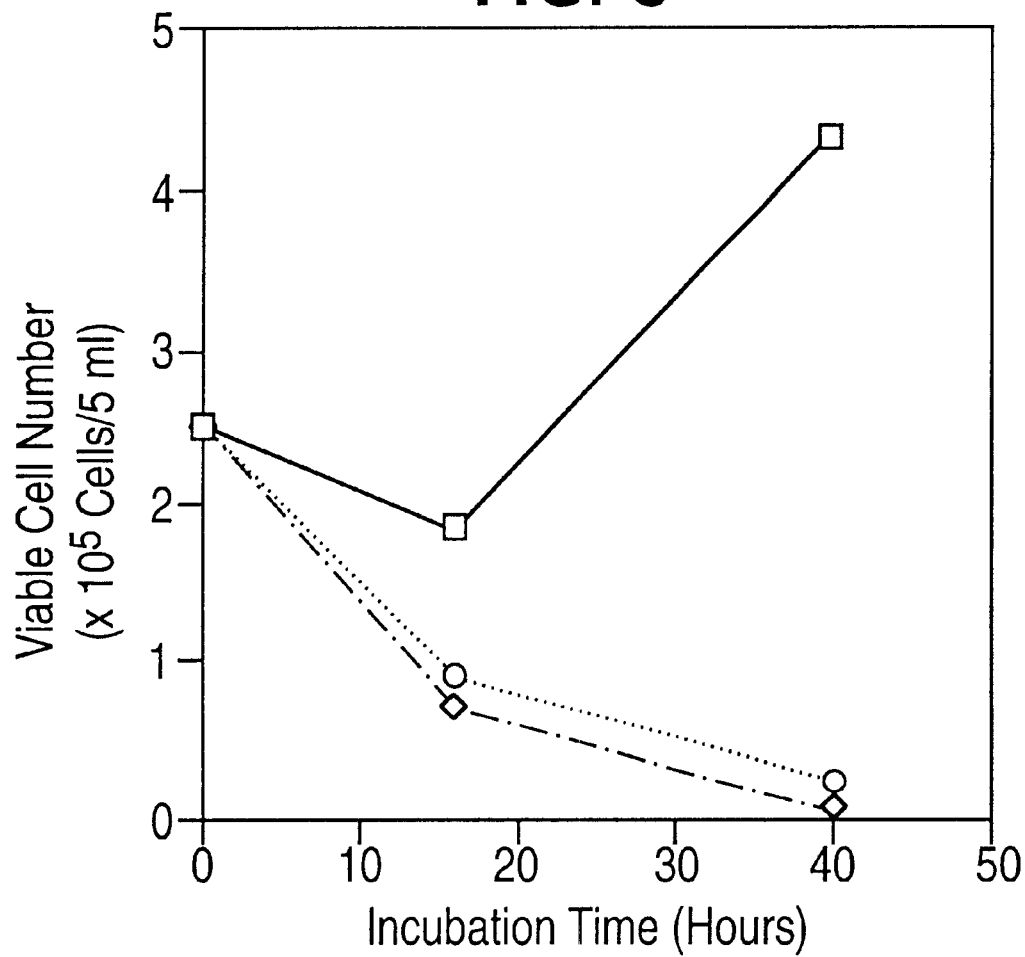
FIG. 5 shows an action to cancer cells of the heat-treated products of uronic acids.

The results are shown in FIG. 5. Thus, FIG. 5 shows the relationship between the incubation time and the viable cell number in the culture medium when the heat-treated galacturonic acid solution or the heat-treated glucuronic acid were added to a culture medium of HL-60 cells to make the concentration of the acids 1 mg/ml wherein the abscissa stands for the incubation time (hours) while the ordinate stands for the viable cell number ($\times 10^5$ cells/5 ml) in the culture medium. In FIG. 5, open square stands for the control where no sample was added, open rhombus stands for the case where the heat-treated galacturonic acid was added and open circle stands for the case where the heat-treated glucuronic acid was added. Thus, both of the heat-treated products exhibited an anticancer action.

(2) Galacturonic acid was dissolved in 50 mM HEPES buffer (pH: 7.0) containing 120 mM of NaCl to make the acid concentration 10 mg/ml. The solution was adjusted to pH 7.0 and to pH 8.0 with 1N NaOH. Each of them was heated at 121 ° C. for 20 minutes and then adjusted to pH 7.0 with 1N NaOH. Apoptosis inducing activity of those samples to HL-60 cells was measured by the method of Example 2 whereupon the sample heated at pH 7.0 showed stronger activity than that heated at pH 8.0.

Figure 6:
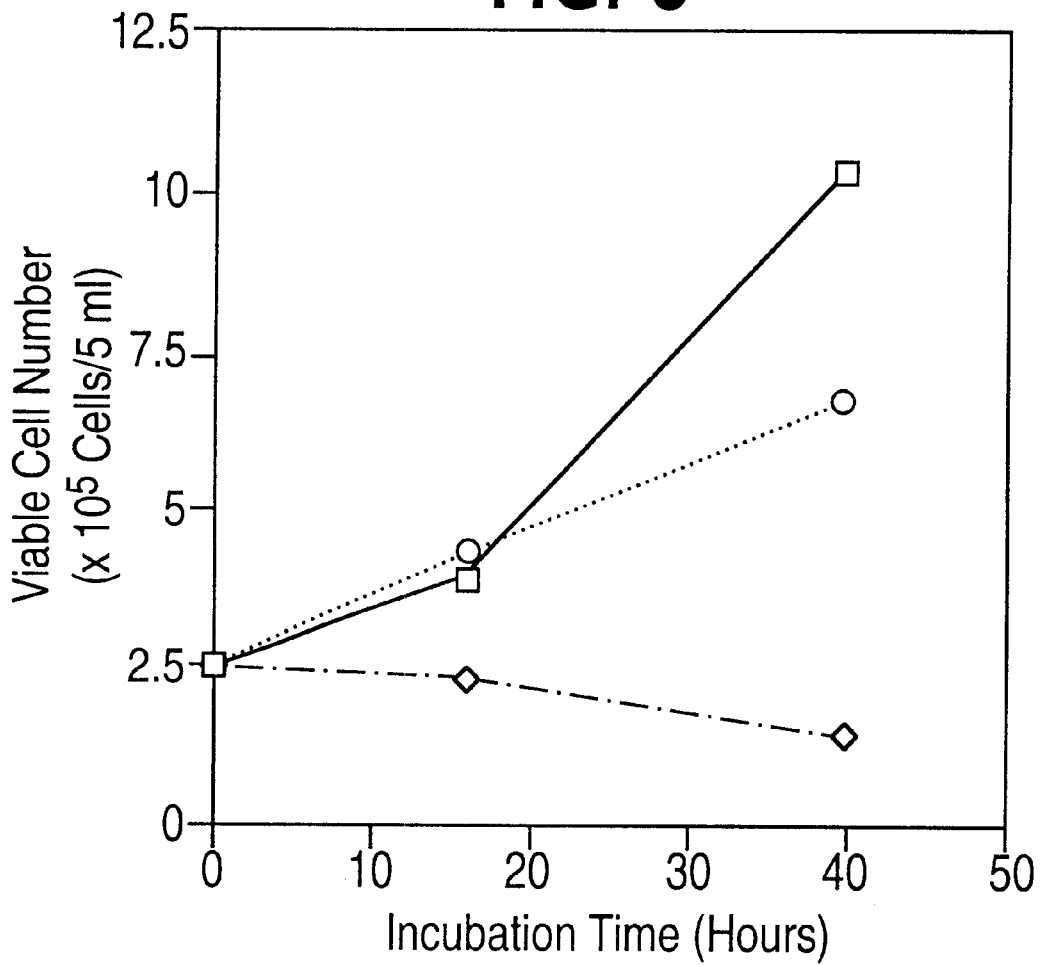
FIG. 6 shows a relation between the pH when uronic acid is heated and the action of the heat-treated product to cancer cells.

The results are shown in FIG. 6. Thus, FIG. 6 shows the relationship between the incubation time and the viable cell number in the culture medium when the heat-treated solutions of galacturonic acid at pH 7.0 or 8.0 were added to make the concentration 1 mg/ml wherein the abscissa stands for the incubation time (hours) while the ordinate stands for the viable cell number ($\times 10^5$ cells/5 ml) in the culture medium. In FIG. 6, open square stands for the control where no sample was added, open rhombus stands for the case where the galacturonic acid heated at pH 7.0 was added and open circle stands for the case where the galacturonic acid heated at pH 8.0 was added. Thus, the product heated at pH 7.0 showed an anticancer activity.

Example 6

Pectin manufactured from apple was dissolved in 50 mM HEPES buffer (pH: 7.0) containing 120 mM of NaCl to make the pectin concentration 10 mg/ml and the solution was heated at 121° C. for 20 minutes to give a heat-treated sample 1. This was dialyzed against 50 mM HEPES buffer (pH: 7.0) containing 120 mM of NaCl using above-mentioned cellulose dialyzing membrane to prepare an inner liquid sample 2. The inner liquid sample 2 after the dialysis was further heated at 121 ° C. for one hour followed by adjusting to pH 7.0 with1N NaOH to prepare a re-heated sample 3.

Each of the samples 1–3 were adjusted to pH 7.0 with 1N NaOH and an apoptosis-inducing activity to HL-60 cells of them was measured by the method of Example 2 whereupon it was found that the samples 1 and 3 showed the activity while, in the case of the sample 2, the activity decreased.

It is clear from those results that the inner liquid of the heat-treated pectin after dialysis having a decreased activity due to the dialysis recovers its activity by means of the re-heating.

Example 7

Commercially available pectin manufactured from apple was dissolved in1N HCl to make the pectin concentration 10 mg/ml and the solution was heated at 121° C. for 1.5 hours to prepare a heat-treated product. Then said heat-treated product was adjusted to pH 7.0 with NaOH and its apoptosis-inducing activity to human promyelocytic leukemia cells (HL-60) was measured as follows.

Thus, HL-60 (ATCC CCL-240) were incubated in an RPMI 1640 medium (manufactured by Nissui) containing 10% of fetal calf serum (manufactured by Gibco) treated at 56° C. for 30 minutes and then suspended in an RPMI 1640 medium to make the cell concentration $2.5 \times 10^5$ cells/4.5 ml.

To 4.5 ml of this suspension was added 0.5 ml of the above-mentioned heat-treated pectin solution and the mixture was incubated at 37° C. for 16 hours in the presence of 5% of carbon dioxide. For the sake of confirmation, the same incubation as above was conducted except that 0.05 ml of an aqueous solution (0.1 mg/ml) of actinomycin D (manufactured by Sigma) which was known as an apoptosis-inducing reagent and 0.45 ml of a physiological saline solution were used instead of the above-mentioned heat-treated pectin solution.

The incubated cells were observed under an optical microscope whereupon condensation of nuclei, contraction of cells and production of apoptotic body were confirmed in both of the heat-treated pectin solution and the actinomycin D-added incubated cells. Incidentally, in the control where the cells to which 0.5 ml of a physiological saline solution was added were incubated, such phenomena were not observed.

Further, to the cell suspension was added twice as much by volume of a 0.4% aqueous solution of trypan blue and an observation was conducted under an optical microscope whereby trypan blue was excreted and colorless cells and blue-colored cells were counted as viable and dead cells, respectively.

Figure 7:
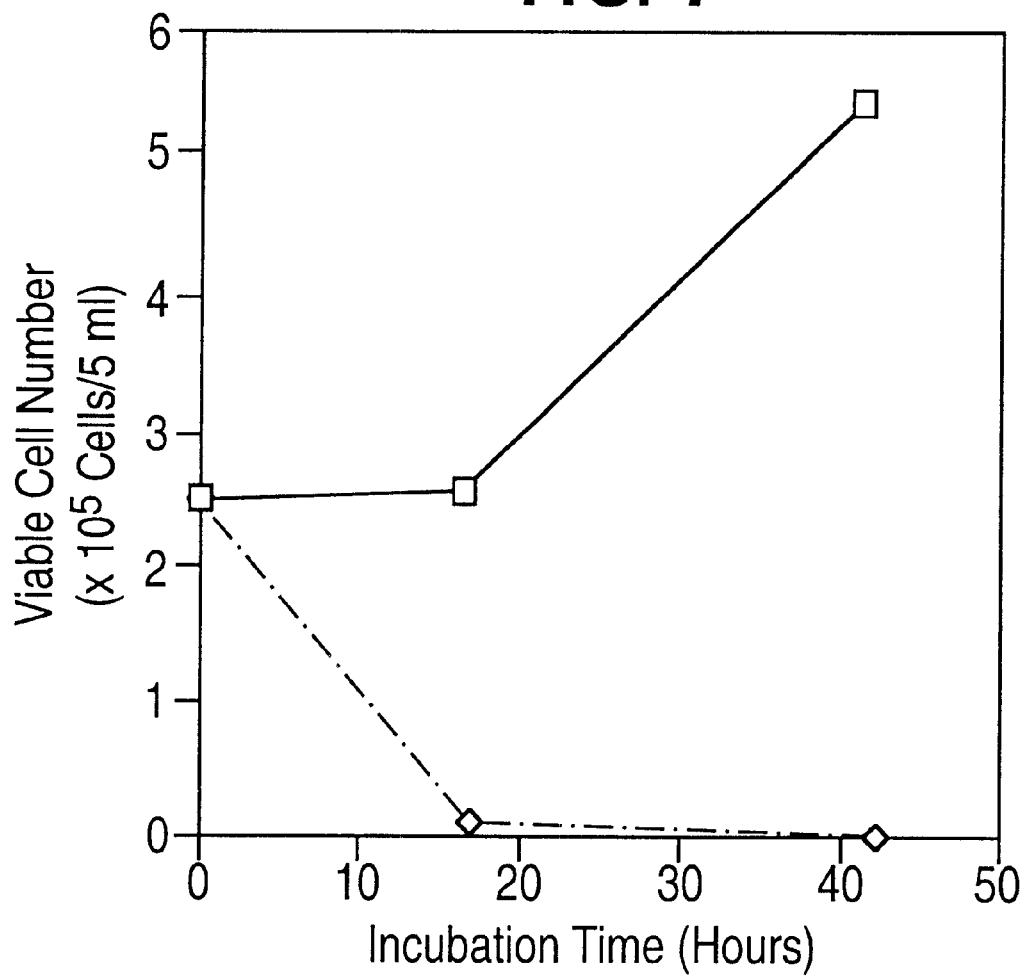
FIG. 7 shows an action to cancer cells of a product obtained by heating pectin under an acidic condition.

The results are shown in FIG. 7. Thus, FIG. 7 shows the relationship between the incubation time and the viable cell number in the culture medium when the heat-treated pectin solution was added to the culture medium of HL-60 cells to make the pectin concentration 1 mg/ml wherein the abscissa stands for the incubation time (hours) while the ordinate stands for the viable cell number ($\times 10^5$ cells/S ml) in the culture medium. In FIG. 7, open square stands for the control where no sample was added and open rhombus stands for the case where the heat-treated pectin solution was added. Thus, the heat-treated pectin showed an anticancer activity.

Example 8

Commercially available pectin manufactured from apple was dissolved in water to make the pectin concentration 10 mg/ml and the solution was adjusted to pH 7.0 with NaOH and heated at 121° C. for one hour. The pH after the heating was 4.5. Then this heat-treated product was adjusted to pH 7.0 with NaOH again, insoluble matters therein were removed by means of a centrifugation (10,000×g for ten minutes) and of a filtration using a filter of 0.22 μm, then ethanol of the same volume was added thereto, the mixture was centrifuged (10,000×g for ten minutes), each of the resulting supernatant fraction and precipitate fraction was evaporated to dryness in vacuo and each of them was dissolved in water of the amount which was same as that used for dissolving the pectin in the initial stage. Each of the aqueous solutions of the ethanol-treated supernatant fraction and of the precipitate fraction was adjusted to pH 7.0 with NaOH and 0.5 ml of each of them was added to 4.5 ml of a culture medium of HL-60 cells to measure the apoptosis-inducing activity by the method of Example 7.

Figure 8:
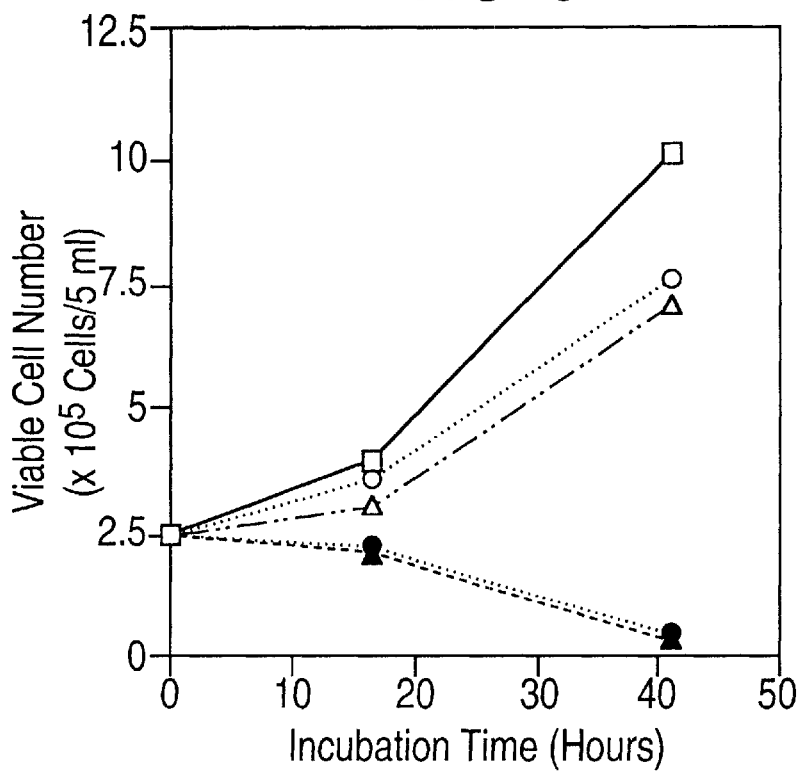
FIG. 8 shows an action to cancer cells of a fraction obtained by solvent extraction of a product obtained by heating pectin under an acidic condition.

As a result thereof, it was found that the apoptosis-inducing activity to HL-60 cells was present in the supernatant fraction. The same result was obtained when 2-propanol was used instead of ethanol. The results are shown in FIG. 8. Thus, FIG. 8 shows the relationship between the incubation time and the viable cell number in the culture medium when the aqueous solution of the supernatant fraction or the precipitate fraction after treating with ethanol or with 2-propanol was added to the culture medium of HL-60 cells wherein the abscissa stands for the incubation time (hours) while the ordinate stands for the viable cell number ($\times 10^5$ cells/5 ml) in the culture medium. In FIG. 8, open square stands for the control where no sample was added, open circle stands for the case where the ethanol-treated precipitate fraction was added, closed circle stands for the case where the ethanol-treated supernatant fraction was added, open triangle stands for the case where the 2-propanol-treated precipitate fraction was added and closed triangle stands for the case where the 2-propanol-treated supernatant fraction was added. Thus, the solvent-treated supernatant fractions showed an anticancer activity.

Samples were prepared by the same method as mentioned above by changing the amount of ethanol or 2-propanol to be added to the heat-treated pectin to 0.5, 1.5 and 2-fold by volume whereupon it was found that, like in the cases where the equivalent volume of ethanol or 2-propanol was added, the activity was noted in the supernatant fractions. Incidentally, the apoptosis-inducing activity was measured by the following method. Thus, to each of the wells of a 96 well microtiter plate were added 100 microliters of an RPMI 1640 medium containing 10% of fetal bovine serum containing 5,000 HL-60 cells, 10 microliters of the sample and 10 microliters of alamarBlue (manufactured by Alamar Bioscience) and incubation was conducted at 37° C. for 48 hours in the presence of 5% of carbon dioxide gas. After that, the value obtained by subtracting the absorbance at 590 nm from that at 560 nm was measured and this was defined as a degree of proliferation of the cells.

Example 9

Commercially available pectin manufactured from apple was dissolved in a 0.1M carbonate buffer to make the pectin concentration 10 mg/ml and the pH was adjusted to 9.5. This solution was heated at 121° C. for 30 minutes. The pH of the heat-treated product was 9.2. Then a part of the heat-treated product was adjusted to pH 7.0 with HCl (sample A) while the remainder was adjusted to pH 4.5. The sample adjusted to pH 4.5 was heated again at 121° C. for 30 minutes and the pH was adjusted to pH 7.0 (sample B). The apoptosis-inducing activity of the samples A and B to HL-60 cells was measured by the method of Example 7 whereupon it was found that sample A did not show the activity while sample B (heat-treated pectin solution II) showed the activity.

Figure 9:
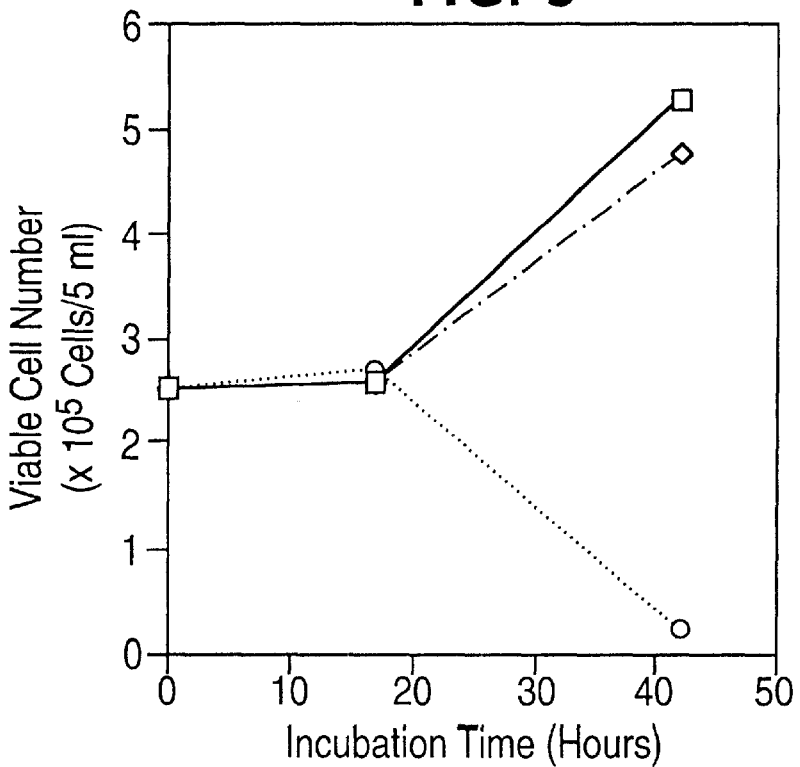
FIG. 9 shows an action to cancer cells of a product obtained by heating pectin firstly under an alkaline condition and then under an acidic condition.

The results are shown in FIG. 9. Thus, FIG. 9 shows the relationship between the incubation time and the viable cell number in the culture medium when sample A or B was added to the culture medium of HL-60 cells wherein the abscissa stands for the incubation time (hours) while the ordinate stands for the viable cell number ($\times 10^5$ cells/5 ml) in the culture medium. In FIG. 9, open square stands for the control where no sample was added, open rhombus stands for the case where the sample A was added and open circle stands for the case where the sample B was added. Thus, the heat-treated pectin solutions showed the anticancer activity.

Example 10

(1) When D-α-galacturonic acid was dissolved in water to make the concentration 10 mg/ml whereupon the pH was 2.4. This was heated at 121° C. for 20 minutes. The pH of the heat-treated product was 2.2. The pH of this heat-treated product was adjusted to pH 7.0 and the apoptosis-inducing activity to HL-60 cells was measured by the method of Example 7 with an exception that the cell suspension in which HL-60 cell numbers were adjusted to $3\times10^5$ cells/4.5 ml was used whereby the present sample was found to have the activity.

Figure 10:
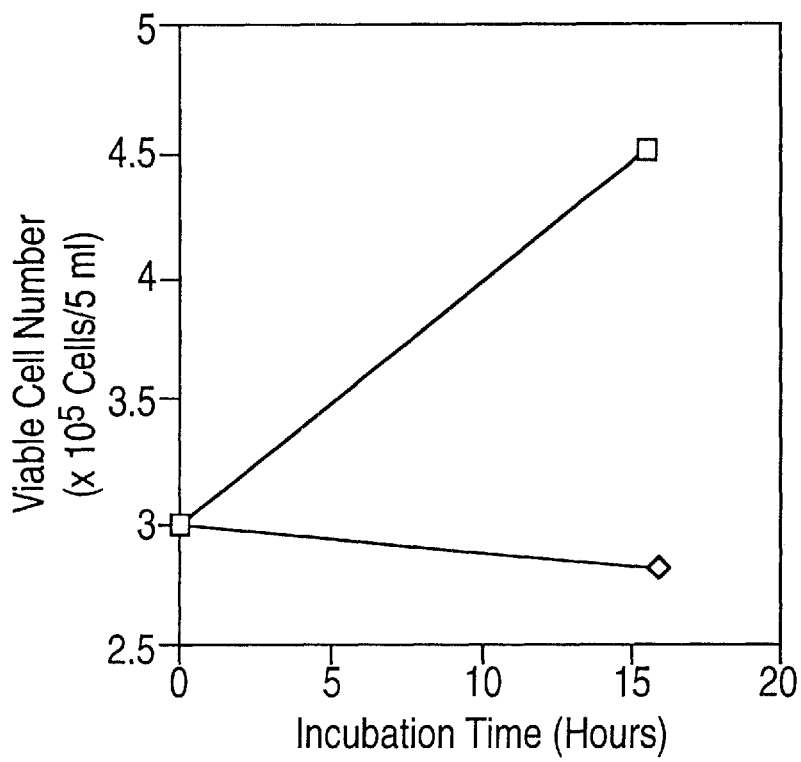
FIG. 10 shows an action to cancer cells of a product obtained by heating galacturonic acid under an acidic condition.

The results are shown in FIG. 10. Thus, FIG. 10 shows the relationship between the incubation time and the viable cell number in the culture medium when the heat-treated product of galacturonic acid under an acidic condition was added to a culture medium of HL-60 cells to make the concentration 1 mg/ml wherein the abscissa stands for the incubation time (hours) while the ordinate stands for the viable cell number ($\times 10^5$ cells/5 ml) in the culture medium. In FIG. 10, open square stands for the control where no sample was added and open rhombus stands for the case where the heat-treated galacturonic acid was added. Thus, the heat-treated product showed the anticancer activity.

(2) D-Glucuronic acid was added to 50 mM HEPES buffer (pH: 7.0) containing 120 mM of NaCl to make the concentration 10 mg/ml whereupon the pH was 3.18. The solution was heated at 121° C. for 20 minutes, pH of the heat-treated solution was adjusted to 7.0 with NaOH and the apoptosis-inducing activity to HL-60 cells was measured by the method of Example 7 whereupon the present sample was found to have the activity.

Figure 11:
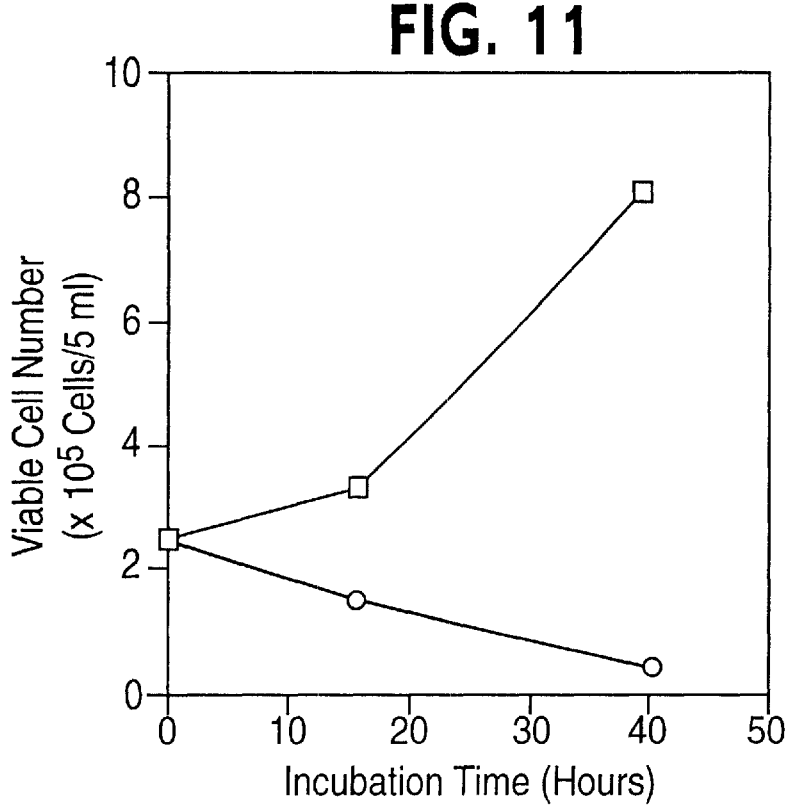
FIG. 11 shows an action to cancer cells of a product obtained by heating glucuronic acid under an acidic condition.

The results are shown in FIG. 11. Thus, FIG. 11 shows the relationship between the incubation time and the viable cell number in the culture medium when heat-treated glucuronic acid was added to the culture medium of HL-60 cells to make the concentration 1 mg/l ml wherein the abscissa stands for the incubation time (hours) while the ordinate stands for the viable cell number ($\times 10^5$ cells/5 ml) in the culture medium. In FIG. 11, open square stands for the control where no sample was added while open circle stands for the case where the heat-treated glucuronic acid was added. Thus, the heat-treated glucuronic acid product showed the anticancer activity.

Example 11

When Dα-galacturonic acid was dissolved in water to make the concentration 1% whereupon the pH was 2.4. When this solution was heated at 121° C. for 20 minutes, pH of the heat-treated solution was 2.2. This was concentrated to an extent of 40-fold in vacuo and 20 microliters of the concentrate was subjected to a high-performance liquid chromatography using a column of Palpak Type S (4.6×250 mm; manufactured by Takara Shuzo). Then the galacturonic acid which was heated under an acidic condition was separated therefrom using an aqueous solution of acetonitrile at the flow rate of 1 ml/minute. During the first 30 minutes, a 90% solution was used and, during the succeeding 20 minutes, a linear concentration gradient was applied using 90% to 50% solutions. Fractionation was conducted every 90 seconds, each fraction was evaporated to dryness in vacuo, then was dissolved in 80 microliters of water and each 10 microliters of the solution were subjected to a measurement of the apoptosis-inducing activity to HL-60 cells by an MTT method which will be given below.

As a result thereof, the activity was found in the two fractions having eluting times of 4.5–12 minutes and 45–48 minutes.

MTT Method: Each of 5 microliters of the diluted solution of each sample liquid or 5 microliters of water was placed in the well of a 96 well microtiter plate. To it was added 100 microliters of an RPMI 1640 medium containing 10% of fetal bovine serum containing 5,000 HL-60 cells and an incubation was conducted at 37° C. for 48 hours in the presence of 5% of carbon dioxide gas. After addition of 10 microliters of phosphate buffered saline containing 5 mg/ml of 3-(4,5-dimethylthiazol-2-yl)-2,5-diphenyltetrazolium bromide (MTT; manufactured by Sigma) hereto, the incubation was conducted for 4 hours more and the growth state of the cells was observed under a microscope. On the other hand, 100 microliters of 2-propanol containing 0.04N HCl was added thereto, the mixture was well stirred and the absorbance at 590 nm was measured and used as a degree of proliferation of the cells.

Example 12

(1) Commercially available pectin manufactured from apple was suspended in water to make the pectin concentration 2.5%. The suspension was adjusted to pH 7.0 with NaOH, placed in a dialyzing tube whose fractionating molecular weight is 12,000–14,000 and dialyzed against 15-fold by volume of water for four times. After being dialyzed, the solution was adjusted to pH 7.0 again and heated at 121° C. for one hour to prepare a heat-treated solution. The pH of this heat-treated solution was 5.4. The pH of this heat-treated solution was adjusted to 7.0 with NaOH, subjected to a centrifugation to remove the insoluble matters and subjected to filtration using the filters of 0.8 micrometer, 0.45 micrometer and 0.22 micrometer in this order to prepare a filter-treated solution. Then this filter-treated solution was filtered through an ultrafiltration membrane with a fractionating molecular weight of 10,000. The filtrate passing through the ultrafiltration membrane was concentrated and evaporated to dryness in vacuo and the dried product was dissolved in water of the amount which was 1/40 of that used for dissolving the pectin in the initial step whereupon a heat-treated pectin solution was prepared.

The heat-treated pectin solution was applied to a column of TOYOPEARL HW-40C (4.4×92 cm; manufactured by Toso) equilibrated with water, a gel filtration was conducted at a flow rate of 2.5 ml/minute and the apoptosis-inducing activity of each of the fractions was measured by the method wherein alamarBlue was used as mentioned in Example 8. As a result, a fraction which was eluted during the eluting time of 448–472 minutes showed the activity.

(2) Dα-Glalacturonic acid was dissolved in water to make the concentration 1% and the solution was adjusted to 7.0 with NaOH. This was heated at 121° C. for 20 minutes and an apoptosis-inducing activity of this heat-treated solution to HL-60 cells was measured by the method of Example 7 whereupon the heat-treated product showed the apoptosis-inducing activity.

Example 13

Pectin (manufactured by Wako Pure Chemicals; code 167–00542), alginic acid (nonswelling; manufactured by Wako Pure Chemicals; code 011–13341), Dα-galacturonic acid (manufactured by Nacalai Tesque; code 165–18) or D-glucuronic acid (manufactured by Nacalai Tesque; code 169–28) was dissolved in distilled water to prepare a solution to make the concentration 1%. In the case of pectin, another solution by dissolving in an aqueous solution of 1N acetic acid was prepared as well.

Each of those 1% solutions was heated at 121° C. for 30 minutes, 1 hour, 2 hours, 4 hours and 16 hours and each of the heated solutions was adjusted to pH 7 with NaOH and subjected to a sterilization by means of a filter of 0.22 micrometer to prepare a sample for measuring the apoptosis-inducing activity.

The samples prepared as such were diluted to an extent of 2, 5, 10, 20, 50 and 100-fold and their apoptosis-inducing activity was assayed by an MTT method mentioned in Example 11 followed by comparing the resulting activities. The results are given in Tables 1–5.

(A) The pH of the 1% aqueous solution of pectin was 3.4. The activity of the heat-treated pectin was shown in terms of the maximum dilutions where the activity was still noted. As shown in Table 1, the activity was significantly increased by the heating treatment at 120° C. for four hours.

TABLE 1

Heat Treatment of Aqueous Solution of Pectin

| Heating Time | pH before Heating | pH after Heating | pH after Adjustment | Activity (Max. Diln.) |
|---|---|---|---|---|
| 2 hrs | 3.4 | 3.3 | 7.0 | 2-fold |
| 4 hrs | 3.4 | 3.2 | 7.2 | 10-fold |
| 16 hrs | 3.4 | 3.5 | 7.0 | 20-fold |

(B) The pH of pectin in a 1% aqueous solution of acetic acid was 2.6. The activity of the solution of pectin in the acetic acid solution was given in terms of the maximum dilution where the activity was still noted. As shown in Table 2, the activity was significantly increased by heating at 120° C. for 16 hours.

TABLE 2

Heat Treatment of Pectin-Acetic Acid Solution

| Heating Time | pH before Heating | pH after Heating | pH after Adjustment | Activity (Max. Diln.) |
|---|---|---|---|---|
| 2 hrs | 2.6 | 2.7 | 7.0 | 2-fold |
| 4 hrs | 2.6 | 2.6 | 7.2 | 5-fold |
| 16 hrs | 2.6 | 2.8 | 7.1 | 20-fold |

(C) The pH of the aqueous solution of galacturonic acid before heating was 2.5. The activity of the heat-treated galacturonic acid was shown in terms of the maximum dilution where the activity was still noted. As shown in Table 3, the activity was significantly increased by heating at 120° C. for one hour.

TABLE 3

Heat Treatment of Aqueous Solution of Galacturonic Acid

| Heating Time | pH before Heating | pH after Heating | pH after Adjustment | Activity (Max. Diln.) |
|---|---|---|---|---|
| 30 min | 2.5 | 2.4 | 6.8 | 2-fold |
| 1 hr | 2.5 | 2.4 | 6.9 | 10-fold |
| 2 hrs | 2.5 | 2.4 | 6.9 | 20-fold |
| 4 hrs | 2.5 | 2.4 | 6.8 | 50-fold |
| 16 hrs | 2.5 | 2.6 | 6.9 | 100-fold |

(D) The pH of an aqueous solution of glucuronic acid before heating was 2.4. The activity of the heat-treated glucuronic acid was given in terms of the maximum dilution where the activity was still noted. As shown in Table 4, the activity significantly increased by heating at 120° C. for 30 minutes.

TABLE 4

Heat Treatment of Aqueous Solution of Glucuronic Acid

| Heating Time | pH before Heating | pH after Heating | pH after Adjustment | Activity (Max. Diln.) |
|---|---|---|---|---|
| 30 min | 2.4 | 2.6 | 6.9 | 10-fold |
| 1 hr | 2.4 | 2.7 | 6.9 | 20-fold |
| 2 hrs | 2.4 | 2.7 | 6.9 | 50-fold |
| 4 hrs | 2.4 | 2.6 | 7.0 | 100-fold |
| 16 hrs | 2.4 | 2.8 | 7.0 | 100-fold |

(E) The pH of an aqueous solution of alginic acid before heating was 3.3. The activity of the heat-treated alginic acid was given in terms of the maximum dilution where the activity was still noted. As shown in Table 5, the activity significantly increased by heating at 120° C. for two hours.

TABLE 5

Heat Treatment of Aqueous Solution of Alginic Acid

| Heating Time | pH before Heating | pH after Heating | pH after Adjustment | Activity (Max. Diln.) |
|---|---|---|---|---|
| 1 hr | 3.3 | 2.6 | 6.8 | 2-fold |
| 2 hrs | 3.3 | 2.5 | 6.9 | 10-fold |
| 4 hrs | 3.3 | 2.7 | 7.0 | 10-fold |
| 16 hrs | 3.3 | 2.9 | 7.3 | 20-fold |

Example 14

Ethanol-washed pectin (manufactured by Wako Pure Chemicals; code 167–00542) (washed with 80% ethanol, washed with 50% ethanol, washed with 80% ethanol and finally washed with 100% ethanol followed by drying in vacuo to give a roughly purified pectin in a powdery form), unwashed pectin (manufactured by Wako Pure Chemicals; code 167–00542), alginic acid (nonswelling; D-mannuronic acid type; manufactured by Wako Pure Chemicals; code 011–13341), alginic acid (swelling; L-guluronic acid type; manufactured by Wako Pure Chemicals; code 014–13331), D-glucuronic acid (manufactured by Nacalai Tesque; code 169–28) or D-α-galacturonic acid (manufactured by Nacalai Tesque; code 165–18) in an amount of 0.5 g was placed in ten test tubes (one test tube being unheated used as a control) and heated in air at 120° C., 150° C. or 180° C. under a dry condition checking the color change of the sample. Depending upon the color change, samplings were conducted at three points and the active ingredient was extracted by the following method.

Thus, each of the dry samples prepared as such was suspended in 12.5 ml of 50% ethanol. The suspension was shaken at room temperature for 16 hours and centrifuged to give an extract. The extract was concentrated and dried in vacuo and re-dissolved in distilled water to make the concentration 1% based upon the amount of the initial sample. The pH of the resulting solution was adjusted to around 7 and sterilized by a filter of 0.22 micrometer to prepare a sample for the activity measurement. The resulting sample was assayed for the activity by an MTT method mentioned in Example 11. The results are given in Tables 6–11 together with dry heating temperature, time, pH upon the re-dissolution and pH after the adjustment. Incidentally, the same operation was conducted for the unheated sample as well but no activity was note Tables 6–11, the activity is given in terms of the degree of dilution of the sample which still exhibited the activity.

From those results, it was found that the active substance was produced by means of a dry heating as well.

TABLE 6

Heat Treatment of EtOH-Washed Pectin

| Dry Heating Temp (° C.) | Time (min) | pH Upon Re-Dissolution | pH after Adjustment | Activity (Deg of Diln) |
|---|---|---|---|---|
| 180 | 60 | 3.7 | 6.9 | 1 |
| 180 | 120 | 3.5 | 6.8 | 1 |

TABLE 7

Heat Treatment of Pectin

| Dry Heating Temp (° C.) | Time (min) | pH Upon Re-Dissolution | pH after Adjustment | Activity (Deg of Diln) |
|---|---|---|---|---|
| 180 | 120 | 3.9 | 7.0 | 1 |

TABLE 8

Heat Treatment of Alginic Acid (D-Mannuronic Acid Type)

| Dry Heating Temp (° C.) | Time (min) | pH Upon Re-Dissolution | pH after Adjustment | Activity (Deg of Diln) |
|---|---|---|---|---|
| 150 | 40 | 3.0 | 6.8 | 1 |
| 150 | 60 | 3.0 | 6.8 | 1 |
| 180 | 20 | 3.0 | 6.8 | 1 |
| 180 | 30 | 3.0 | 6.8 | 1 |
| 180 | 40 | 3.1 | 6.9 | 1 |

TABLE 9

Heat Treatment of Alginic Acid (L-Guluronic Acid Type)

| Dry Heating Temp (° C.) | Time (min) | pH Upon Re-Dissolution | pH after Adjustment | Activity (Deg of Diln) |
|---|---|---|---|---|
| 150 | 60 | 3.3 | 6.7 | 1 |
| 180 | 20 | 3.3 | 6.7 | 1 |
| 180 | 30 | 3.3 | 6.7 | 1 |
| 180 | 40 | 3.2 | 6.8 | 1 |

TABLE 10

Heat Treatment of Glucuronic Acid

| Dry Heating Temp (° C.) | Time (min) | pH Upon Re-Dissolution | pH after Adjustment | Activity (Deg of Diln) |
|---|---|---|---|---|
| 150 | 20 | 3.2 | 6.8 | 1 |
| 150 | 30 | 3.3 | 6.9 | 1 |
| 150 | 40 | 3.3 | 6.9 | 1 |
| 180 | 10 | 3.1 | 7.0 | 1 |
| 180 | 20 | 3.3 | 6.8 | 1 |
| 180 | 30 | 3.3 | 6.9 | 2 |

TABLE 11

Heat Treatment of Galacturonic Acid

| Dry Heating Temp (° C.) | Time (min) | pH Upon Re-Dissolution | pH after Adjustment | Activity (Deg of Diln) |
|---|---|---|---|---|
| 120 | 60 | 2.9 | 6.9 | 1 |
| 120 | 120 | 2.9 | 6.9 | 1 |
| 150 | 20 | 2.9 | 6.8 | 2 |
| 150 | 30 | 2.9 | 6.9 | 2 |
| 150 | 40 | 2.9 | 6.8 | 2 |
| 180 | 10 | 2.9 | 7.1 | 2 |
| 180 | 20 | 2.9 | 6.8 | 2 |
| 180 | 30 | 2.9 | 6.8 | 1 |

Example 15

Commercially available pectin manufactured from apple was dissolved in water to make the concentration 1% and the solution was placed in a pear-shaped flask equipped with a refluxing condenser and heated in an oil bath kept at 110–120° C. for 18 hours, 42 hours or 66 hours. Temperature of the pectin solution during the heating was 100–102° C.

The resulting pectin solution was centrifuged to remove the precipitate and the supernatant was diluted with water to an extent of three- or ten-fold to prepare a sample. The diluted sample (10 microliters) and 100 microliters of an RPMI 1640 medium containing 10% of fetal bovine serum containing 5,000 HL-60 cells were added to a well of a 96 well microtiter plate and incubated at 37° C. for 48 hours in the presence of 5% carbon dioxide gas and the activity was measured by an MTT method mentioned in Example 11.

The results were that no viable cell was found in the sections to which the three-fold diluted solution of pectin heated for 18 hours and also to which the three- and ten-fold diluted solutions of pectin heated for 42 and 66 hours whereby, at the concentrations of such degrees of dilution, the pectin heated at 100° C. showed the activity.

On the other hand, in the section to which ten-fold diluted solution of pectin heated for 18 hours was added, nearly all cells were viable but, when compared with the control which was a section to which water was added, the absorbance at 590 nm was lower.

Example 16

Pomosin pectin LM-13CG (manufactured by Hercules) (5 kg) was added to 100 liters of tap water, steam was blown thereinto for 35 minutes so that the liquid temperature was raised from 28° C. to 120° C. and the liquid was kept at 120° C. for five hours with stirring and cooled to give 135 liters of a cooled liquid. To this cooled liquid were added 1.35 kg of Celite #545 (manufactured by Celite) and 1.35 kg of Silica #600-S (manufactured by Chuo Silica) as filter aid and the mixture was filtered through a compact filter (Advantec #327; with a 6-inch filter paper in 16 stages) precoated with 0.1 kg of Celite #545 and 0.1 kg of Silica #600-S. The resulting filtrate was subjected to a continuous instant heating (at 98° C. for 60 seconds) by a Plate Heater (manufactured by Nichihan Seisakusho) followed by cooling to prepare 150 liters of heat-treated pectin solution I.

The pH, acidity and sugar content of the heat-treated pectin solution I were about 3.5, 6.2 ml and 5.8 Brix %, respectively. Incidentally, the pH was measured by a pH-meter, the acidity was given by the amount (ml) of 0.1N NaOH required for neutralizing 10 ml of the sample to pH 7.0 and the sugar content was measured by a Brix saccharometer.

Activity of the above heat-treated pectin solution I to human promyelocytic leukemia cells (HL-60 cells) was measured as follows.

Thus, HL-60 (ATCC CRL-240) was incubated at 37° C. in an RPMI 1640 medium (manufactured by Nissui) containing 10% of fetal bovine serum (manufactured by Gibco) treated at 56° C. for 30 minutes and suspended in the above medium to make the concentration $2.5 \times 10^5$ cells/4.5 ml. To 4.5 ml of this suspension was added 0.5 ml of the above heat-treated pectin solution diluted with water giving the concentration of 20 mg/ml, 10 mg/ml, 5 mg/ml, 2 mg/ml, 1 mg/ml, 0.5 mg/ml, 0.2 mg/ml or 0.1 mg/ml and the mixture was incubated at 37° C. in the presence of 5% of carbon dioxide gas for 24 or 48 hours.

To the cultured cells was added an aqueous solution of trypan blue, the mixture was allowed to stand at room temperature for several minutes and an observation was conducted under an optical microscope whereby trypan blue was excreted and colorless cells and blue-colored cells were counted as viable and dead cells, respectively. The incubated cells were also observed under an optical microscope whereupon condensation of nuclei, contraction of cells and production of apoptotic body were confirmed in the section to which 1 mg/ml or more heat-treated pectin was added. Incidentally, in the section to which 0.5 mg/ml or less heat-treated pectin was added and in the control where 0.5 ml of water was added, such phenomena were not noted.

Figure 12:
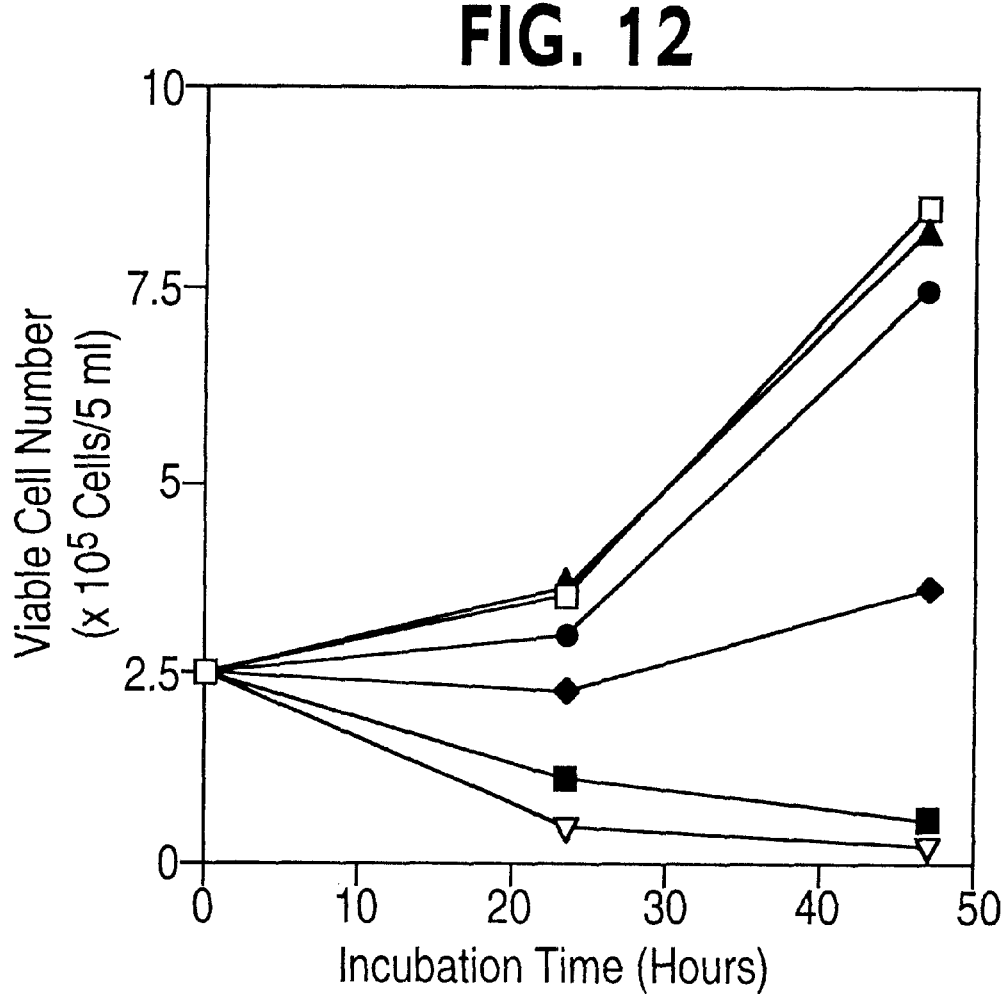
FIG. 12 shows an action of a heat-treated solution I of pectin to cancer cells.

The results are shown in FIG. 12. Thus, FIG. 12 shows the relationship between the incubation time and the viable cell number in the culture medium when the heat-treated pectin solution of various concentrations was added to the culture medium of HL-60 cells wherein the abscissa stands for the incubation time (hours) while the ordinate stands for the viable cell number ($\times 10^5$ cells/5 ml) in the culture medium. In FIG. 12, open square stands for the control where no sample was added, reversed open triangle stands for the case where 2 mg/ml of heat-treated pectin was added, closed square stands for the case where 1 mg/ml of heat-treated pectin was added, closed rhombus stands for the case where 0.5 mg/ml of heat-treated pectin was added, closed circle stands for the case where 0.2 mg/ml of heat-treated pectin was added and closed triangle stands for the case where 0.1 mg/ml of heat-treated pectin was added. Thus, the cases where 50–20 mg/ml of heat-treated pectin was added, the similar activity as in the case where 2 mg/ml of heat-treated pectin was added as shown in a reversed open triangle and, when 1 mg/ml or more of heat-treated pectin was added, an anticancer activity was noted.

Example 17

Commercially available D-glucuronic acid (manufactured by Sigma; G5269) was dissolved in water to make the concentration 1% and the solution was heated at 121° C. for four hours, neutralized to pH 7.0 with NaOH and diluted 10-, 40-, 80- and 160-fold with water. Each of the diluted heat-treated glucuronic acid solution (0.5 ml) was added to 4.5 ml of an RPMI 1640 medium containing 10% of fetal bovine serum containing $2.5 \times 10^5$ HL-60 cells, incubation was conducted at 37° C. for 24 hours in the presence of 5% carbon dioxide gas and an anticancer activity was measured by the method of Example 7 in terms of an activity for inhibiting the proliferation of the cells. As a result, in the sections of 10- to 80-fold diluted solutions were added, a decrease in the cell numbers and the cell survival rate were noted. In the 40- to 80-fold diluted solutions, DNA was found to become low molecules. Incidentally, survival rate (R) of the cell in terms of % was calculated by the following formula.

$R = Vs/(Vs+Ds) \times 100 + Dc/(Vc+Dc) \times 100$

In the formula, Vs and Ds are numbers of vital cells and dead cells, respectively, in the section where the sample was added; and Vc and Dc are numbers of vital and dead cells, respectively, in the section where water was added. The anticancer activity in 1 ml of the medium when R is 50% is defined as one unit.

When the resulting survival rates of cell were plotted to the common logarithmic value of the degree of dilution of the heat-treated glucuronic acid, all points were on one straight line and the survival rate R (%) of the heat-treated glucuronic acid was calculated from the following formula.

$R = 58.656X - 31.884$

[in the formula, X is a degree of dilution of the heat-treated glucuronic acid]

From this straight line, it was found that the nondiluted heat-treated glucuronic acid corresponded to 250 units/ml.

Figure 13:
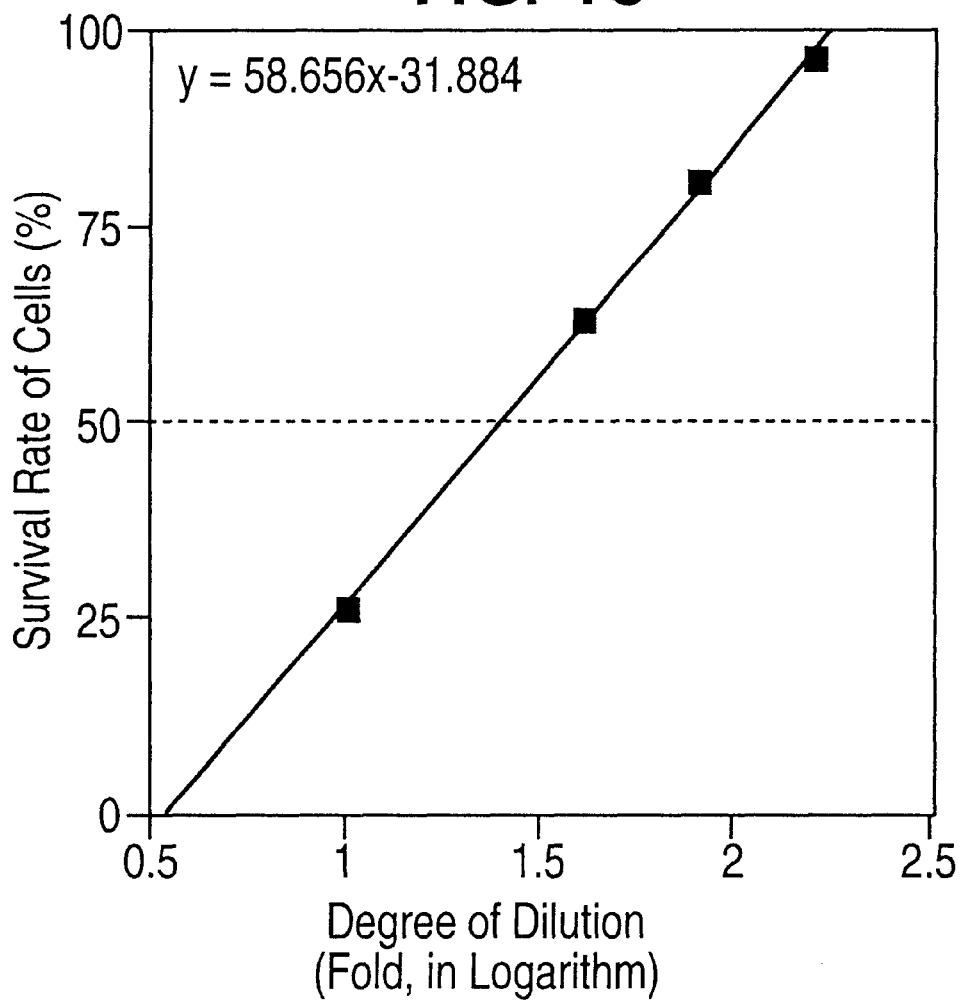
FIG. 13 shows a relation between the dilution rate of a heat-treated product of glucuronic acid and the survival rate of the cells.

The results are shown in FIG. 13. Thus, FIG. 13 shows the relationship between the degree of dilution and the survival rate of the cells in the culture medium when the heat-treated glucuronic acid with various degrees of dilution was added to HL-60 cells followed by incubating for 24 hours. The abscissa stands for the degree of dilution (fold; in logarithm) while the ordinate stands for the survival rate of the cells (%).

Example 18

(1) A 25% solution of puree of peeled rind of apple (manufactured by Maruzen Shokuhin Kogyo), banana puree (manufactured by Ogawa Koryo), green beefsteak plant extract 1/4 (manufactured by Dan Foods), pumpkin extract 60 (manufactured by Dan Foods), minced pumpkin (manufactured by Dan Foods), celery puree (manufactured by Dan Foods), burdock puree (manufactured by Dan Foods) or echalote extract 60 (manufactured by Dan Foods) was prepared. Each of them was heated at 121° C. for 40 minutes. Each of the solution prepared by the same manner was heated at 121° C. for four hours. Each of the heated solutions was cooled and filtered to prepare a heat-treated solution.

Sugar content and pH of the solution heated at 121° C. for 20 minutes are given in Table 12.

TABLE 12

| Starting Material | Sugar Contn (Brix) | pH |
|---|---|---|
| Puree of Peeled Rind of Apple | 3.6 | 3.6 |
| Banana Puree | 6.0 | 5.9 |
| Green Beefsteak Plant Extract 1/4 | 2.2 | 5.8 |
| Pumpkin Extract 60 | 16.8 | 5.3 |
| Minced Pumpkin | 4.0 | 5.7 |
| Celery Puree | 1.6 | 5.5 |
| Burdock Puree | 2.4 | 5.8 |
| Echalote Extract 60 | 15.6 | 4.9 |

Sugar content and pH of the solution heated at C121° C. for four hours are given in Table 13.

TABLE 13

| Starting Material | Sugar Contn (Brix) | pH |
|---|---|---|
| Puree of Peeled Rind of Apple | 3.6 | 3.6 |
| Banana Puree | 5.5 | 4.6 |
| Green Beefsteak Plant Extract 1/4 | 2.5 | 5.3 |
| Pumpkin Extract 60 | 16.6 | 4.7 |
| Minced Pumpkin | 3.0 | 5.0 |
| Celery Puree | 1.6 | 4.9 |
| Burdock Puree | 2.5 | 4.8 |
| Echalote Extract 60 | 13.8 | 4.3 |

In each of the heat-treated solutions, the fractions having a molecular weight of 10,000 or less were found to show an anticancer activity as mentioned in Example 17.

Then sugar content (Brix) was adjusted to 1 and an organoleptic test was conducted for each of the heat-treated solutions whereby all of the heat-treated solutions showed good organoleptic property as food or beverage.

(2) The 25% aqueous solutions of banana puree, apple puree and celery puree heated at 121° C. for four hours were taken as representative examples and their anticancer activity units were measured by the method of Example 17. The results are given in Table 14. Thus, as a result of the heating treatment, anticancer active substance was produced in each of the treated solutions.

TABLE 14

| Puree Used | Activity (units/ml) |
|---|---|
| Banana Puree | 23.4 |
| Apple Puree | 9.5 |
| Celery Puree | 0.5 |

Water (160 ml) was added to 40 g of (1) radish leaves, (2) carrot leaves, (3) carrot, (4) cabbage, (5) eggplant without rind, (6) banana or (7) albedo of hassaku orange and each of the mixtures was homogenized using a mixer. A part of it was heated at 121° C. for four hours and centrifuged and the supernatant thereof was adjusted to pH 6 with NaOH to prepare a sample A while the remainder was adjusted to pH 3 with HCl and heated at 121° C. for four hours and the supernatant after the centrifugation was adjusted to pH 6 with NaOH to prepare a sample B.

Each of the samples A and B prepared from (1)–(7) was diluted and 10 microliters of the diluted solution was subjected to a measurement for anticancer activity by an MTT method mentioned in Example 11. The results are given in Table 15. The data shown in Table 15 are the degrees of dilution where the activity was still noted and the sign "–" shows that no activity was noted in the sections to which nondiluted solution was added. In all of the fruits and the vegetables, generation of the activity was noted in their heat-treated products. In the table, the degrees of dilution are those where the cells were completely killed while the values in parentheses are those where the cells were affected.

TABLE 15

| Vegetables and Fruits Used | Degree of Dilution for | |
|---|---|---|
| | Sample A | Sample B |
| Radish Leaves | 1 (4) | 2 (4) |
| Carrot Leaves | — | 1 |

TABLE 15-continued

| Vegetables and Fruits Used | Degree of Dilution for | |
|---|---|---|
| | Sample A | Sample B |
| Carrot | 2 (4) | 1 (2) |
| Cabbage | 1 (4) | 1 |
| Eggplant | 1 (2) | 1 |
| Banana | 2 (4) | 2 (4) |
| Wave Packet | 4 (8) | 4 (8) |

Example 20

Nonswelling alginic acid (manufactured by Wako Pure Chemicals; 011–13341) or swelling alginic acid (manufactured by Wako Pure Chemicals; 014–13331) was suspended in water to make the concentration 1% whereupon the pH was 3.32 and 3.38, respectively. Each of them was heated at 121° C. for 20 minutes and its anticancer activity was measured as a cell proliferation inhibiting activity to HL-60 cells by the method of Example 7.

Incidentally, the HL-60 cell numbers at the initiation of the incubation were $3 \times 10^5$ cells/5 ml.

Figure 14:
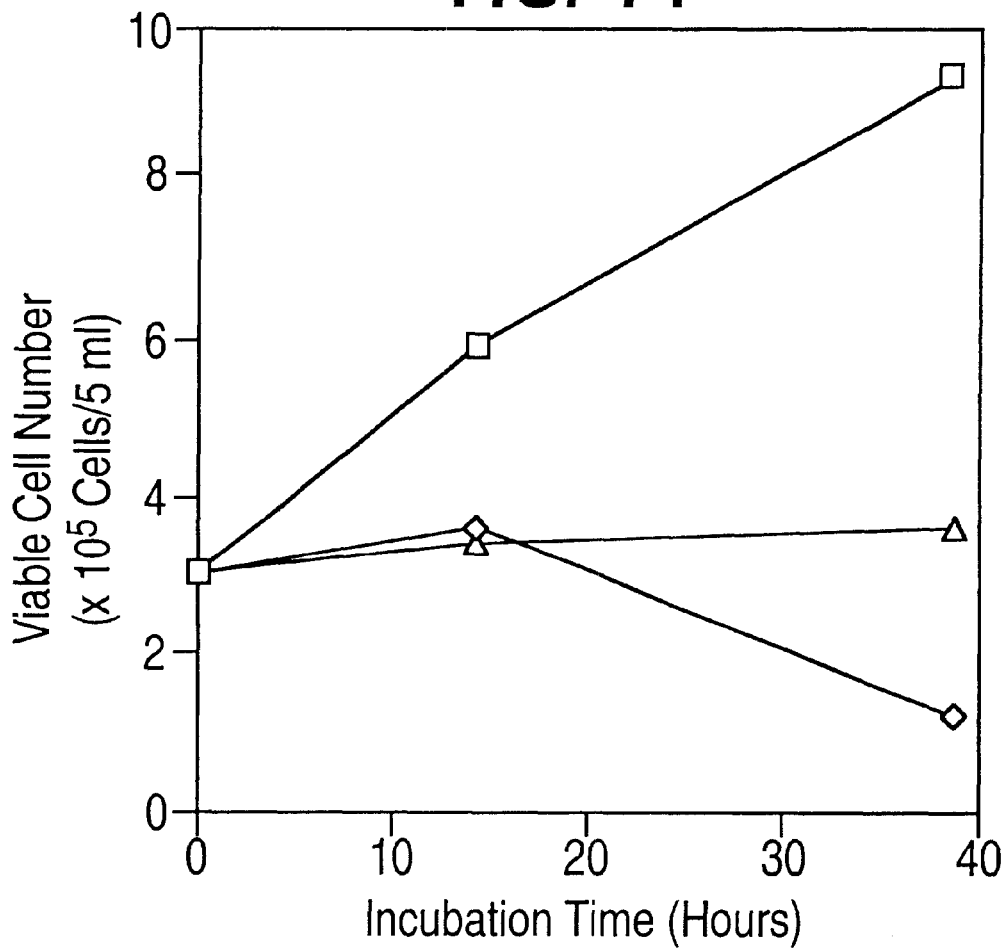
FIG. 14 shows an action of a heat-treated product of alginic acids to cancer cells.

The results are shown in FIG. 14. Thus, FIG. 14 shows the relationship between the incubation time and the viable cell number in the culture medium when the heat-treated nonswelling alginic acid or swelling alginic acid solution was added to the culture medium of HL-60 cells to make the concentration 1 mg/ml. The abscissa stands for the incubation time (hours) while the ordinate stands for the viable cell number ($\times 10^5$ cells/5 ml) in the culture medium. In FIG. 14, open square stands for the control where no sample was added, open rhombus stands for the case where the heat-treated nonswelling alginic acid was added and open triangle stands for the case where the heat-treated swelling alginic acid was added. Thus, a high activity was noted in the heat-treated nonswelling alginic acid.

Example 21

A 1% aqueous suspension of alginic acid HFD (manufactured by Dainippon Pharmaceutical) was prepared and subjected to a heat treatment at 120° C. for four hours. The supernatant of the heat-treated solution after centrifugation was subjected to an anticancer activity measurement by the method mentioned in Example 17 to calculate the anticancer activity unit. The results are shown in Table 16. Thus, generation of an active substance was noted in the heat-treated alginic acid.

TABLE 16

| Heat-Treated Alginic Acid HFD | Activity (Units/ml) |
|---|---|
| Heated 1% Solution | 83.3 |

Example 22

Alginic acid HFD (manufactured by Dainippon Pharmaceutical) (1 g) was suspended in 50 ml of water and heated at 121 ° C. for 30 minutes, 1 hour, 2 hours or 14 hours. Each of the heat-treated solutions was prepared by means of centrifugation and its molecular weight was determined. Determination of the molecular weight was conducted under the following conditions.

Guard Column: TSK Guard Column PWH
Column: TSK Gel G3000PW
Eluting Solution: 0.2M NaCl
Detection: by absorption at 210 nm When the heating time was 30 minutes, 1 hour, 2 hours, 4 hours and 14 hours, the low-molecular weight decomposed products of the molecular weights of 1,800; 1,200 and 630; 1,100 and 630; 1,100 and 630; and 620 and 400 as the main peaks were produced respectively and, at the same time, other low-molecular weight decomposed products were produced as well. Incidentally, no high-molecular weight substances having the molecular weight of 10,000 or more were contained and the anticancer and antibacterial activities were found in the fractions having a molecular weight of 500 or less.

Example 23

(1) Commercially available glucuronolactone (manufactured by Merck; Code No. 100282) was dissolved in water to make the concentration 1% and the solution was heated at 121° C. for 0.5, 1, 2, 4 or 16 hours. The anticancer activity of each of the heated solutions prepared as such was measured by the method of Example 17. In the solution heated for 0.5 hour, production of the anticancer substance was noted. It was found that the longer the heating time, the more the production of the anticancer substance and, in each of the products heated for 4 and 16 hours, the production was about 10-fold of that heated for 0.5 hour.

(2) The above-mentioned glucuronolactone was dissolved in water to make the concentration 0.1%, 1%, 2%, 5%, 10% or 20% and each of the solution was heated at 121° C. for four hours. The anticancer activity of each of the heat treated solutions was measured by the method of Example 17. Although the production of anticancer substance was noted in all of the concentrations, the potency of the anticancer activity of the heat-treated product per the glucuronolactone used was the highest when 0.1% aqueous solution of glucuronolactone was used.

(3) The pH of the above-mentioned 1% aqueous solution of glucuronolactone was adjusted to 1, 2, 3 or 4.5 with HCl or with NaOH and each of the solutions was heated at 121° C. for four hours. The anticancer activity of each of the heat-treated solutions prepared as such was measured by the method of Example 17. Although the production of anticancer substance was noted in all cases of the above pH values, the potency of the anticancer activity of the heat-treated product at pH 3–4.5 was about 15-fold of that at pH 1 per the glucuronolactone used.

(4) Commercially available D-glucuronic acid (manufactured by Sigma; G5269) was dissolved in water to make the concentration 1% and heated at 121° C. for four hours whereby a sample (pH: 2.6) where the pH was not adjusted and another sample where the pH was adjusted to 6.6 with NaOH. Each 1 ml of them was stored at −20° C., 4° C. and 37° C. and the anticancer activity was measured by the method of Example 17.

The result after storing for 25 days was that, when stored at 37° C., the anticancer activity of the heat-treated product was somewhat decreased while, in the case of 4° C. and −20° C., the activity was almost stable.

Example 24

Pomosin pectin type LM-13CG (manufactured by Hercules), alginic acid HFD (manufactured by Dainippon Pharmaceutical), D-glucuronic acid (manufactured by Nacalai Tesque) or glucuronolactone (manufactured by Merck) was dissolved or suspended in water to make the concentration 1% and the solution or the suspension was heated at 95° C., 121° C. or 132° C. for 16 hours. The anticancer activity units of those heat-treated products were measured by the method of Example 17. The results are given in Table 17.

TABLE 17

| Heated Material | Heating Temp (° C.) | Activity (Units/ml) |
| --- | --- | --- |
| Pectin | 95 | 1.2 |
|  | 121 | 32.3 |
|  | 132 | 1.4 |
| Alginic Acid | 95 | 1.0 |
|  | 121 | 57.8 |
|  | 132 | 25.7 |
| Glucuronic Acid | 95 | 40.8 |
|  | 121 | 345 |
|  | 132 | 30.2 |
| Glucuronolactone | 95 | 42.7 |
|  | 121 | 5,376 |
|  | 132 | 33.8 |

Example 25

(1) Apple pectin (1.5 g; manufactured by Wako Pure Chemicals) was suspended in 100 ml of water and the suspension was adjusted to pH 12 with NaOH. This was stirred at 4° C. keeping the pH at 12 by a gradual addition of NaOH. When eight hours elapsed after that, a decrease in pH was not observed. After 24 hours, the suspension was adjusted to pH 5 with HCl, 4-fold by volume of ethanol was added thereto and the mixture was stirred at 4° C. for one hour and filtered through a filter paper. The resulting precipitate was washed with 65% ethanol and then with 99. 5% ethanol followed by drying in vacuo to give 1.32 g of pectic acid.

(2) Pectic acid (200 mg) obtained in the above (1) was dissolved in 200 ml of water and 2 ml of concentrated HCl was gradually added thereto. The mixture was heated at 80° C. for 66 hours and centrifuged at 20,000×g for 30 minutes to give a supernatant and a precipitate. The supernatant was adjusted to pH 7 by NaOH, dialyzed against water using a dialyzing membrane with cutoff molecular weight of 1000 and dried by freezing to give 18.4 mg of an acid-soluble fraction. The precipitate was suspended in 30 ml of water, adjusted to pH 6 by NaOH, dialyzed against water using a dialyzing membrane with cutoff molecular weight of 1000 and freeze-dried to give-114 mg of an acid-insoluble fraction.

(3) Each of the acid-soluble and acid-insoluble fractions obtained in the above (2) was dissolved in water to prepare a 1% solution and the solution was adjusted to pH 3 with HCl and heated at 121° C. for 20 minutes. Anticancer activity of the resulting heat-treated products was determined by measuring an activity for inhibiting the cell proliferation by means of a method using alamarBlue as mentioned in Example 2. As a result, an anticancer activity was noted in the acid-soluble fraction of the heat-treated product.

Example 26

(A) D-Glucuronic acid (manufactured by Nacalai Tesque, code 169–28) was dissolved in distilled water to make the concentration 1%, the solution was heated at 120° C. overnight and the pH was adjusted to around 7 by NaOH. Antibacterial activity of this heat-treated glucuronic acid was investigated as follows.

Thus, the microorganism to be tested was subjected to a seed culture in an L-broth (containing 1% of tryptone, 0.5% of yeast extract and 0.5% of NaCl; pH: 7.0) overnight. A seed-cultured liquid (5 microliters) was inoculated to a medium prepared by adding none of or 50, 100, 250, 500 or 1000 microliters of heat-treated glucuronic acid to 5 ml of L-broth and the culture was incubated at 37° C. with shaking whereupon the growth was observed. At the initiation of the incubation and at eight hours thereafter, turbidity of the culture was measured using a Fuji Digital Turbidimeter (sold by Fuji Kogyo KK; manufactured by Akiyama Denki Seisakusho) under the condition that the adjusting scale was 82.3 and, by means of the value (growth turbidity) obtained by subtracting the value at the initiation stage from the value after eight hours, growth of the test microorganism was determined. Incidentally, in the case of the test organism (6), a brain heart infusion medium was used instead of the L-broth.

The microorganisms tested were Escherichia coli HB 101 (ATCC 33694; test microorganism (1)); Salmonella typhimurium LT-2 (ATCC 27106; test microorganism (2)); Pseudomonas aeruginosa (IFO 3080; test microorganism (3)); Staphylococcus aureus 3A (NCTC 8319; test microorganism (4)); Bacillus subtilis (IFO 3034; test microorganism (5)); and Streptococcus mutans GS5 (a strain stored at the National Institute of Health; test microorganism (6)).

TABLE 18

| | (Growth Turbidity) | | | | |
| --- | --- | --- | --- | --- | --- |
| Test Microorganism | Amount of Heat-Treated Product ($\mu$l/5 ml medium) | | | | |
|  | 0 | 50 | 100 | 250 | 500 |
| (1) | 239 | 183 | 89 | 6 | 10 |
| (2) | 247 | 177 | 36 | 5 | 11 |
| (3) | 273 | 262 | 212 | 237 | 61 |
| (4) | 285 | 251 | 247 | 20 | 11 |
| (5) | 280 | 258 | 205 | 73 | 13 |
| (6) | 140 | 136 | 131 | 125 | 10 |

The heat-treated product showed antibacterial activity to each of the test microorganisms at any of the additions of 100–500 microliters/5 ml. In addition, the heat-treated product showed antibacterial activity to methicillin-resistant Staphylococcus aureus, enterotoxin-productive S. aureus, Bacillus cereus of a vomiting type, B. cereus of a diahhrea type and enterorrhagiac E. coli O-157 as well.

(B) Alginic acid for food additive (Alginic Acid HFD; manufactured by Dainippon Pharmaceutical Co., Ltd. ) was dissolved in distilled water to make the concentration 1% and the solution was heated at 120° C. overnight and adjusted to pH around 7 with NaOH. Like in the above-mentioned method, this heat-treated alginic acid solution was added in an amount of 250 to 1000 microliters and its antibacterial activity to the test microorganisms (1)–(6) was tested. In the case of the test microorganism (6), the solution was added to an extent of 1500 microliters. The results are given in Table 19.

TABLE 19

(Growth Turbidity)

| Test Microorganism | Amount of Heat-Treated Product (μl/5 ml medium) | | | | |
|---|---|---|---|---|---|
| | 0 | 250 | 500 | 1000 | 1500 |
| (1) | 239 | 30 | 8 | 13 | — |
| (2) | 247 | 10 | 8 | 12 | — |
| (3) | 273 | 233 | 188 | 30 | — |
| (4) | 285 | 222 | 12 | 15 | — |
| (5) | 280 | 158 | 22 | 13 | — |
| (6) | 140 | 138 | 130 | 101 | 12 |

The heat-treated product showed antibacterial activity to each of the test microorganisms at any of the additions of 250–1500 microliters/5 ml. In addition, the heat-treated product showed antibacterial activity to methicillin-resistant Staphylococcus aureus, enterotoxin-productive S. aureus, Bacillus cereus of a vomiting type, B. cereus of a diahhrea type and enterorrhagiac E. coli O-157 as well.

Example 27

Commercially available apple pectin (5 g) was dissolved in 500 ml of 200mM NaCl and adjusted to pH 7.0 with NaOH. This solution was heated at 121° C. for 30 minutes and readjusted to pH 7.0 with NaOH. This was centrifuged at 12,000 rpm (about 10,000 g) for 30 minutes and the anticancer action of the re supernatant (hereinafter, referred to as "the sample") was tested.

Murine solid carcinoma Meth A ($4 \times 10^6$ cells/mouse) was subcutaneously injected to the abdominal region of a BALB/c mouse of ten weeks age (female; body weight ca. 20 grams). After that, the sample (100 mg/kg/day) was subcutaneously injected into the same place for consecutive ten days.

On the other hand, a physiological saline solution instead of the sample was subcutaneously injected to the control group in the same manner. After two weeks, the solid carcinoma tissue formed in the abdominal region of the mouse was excised and its weight was measured. The results are given in Table 20. Thus, in the control group, an average weight of the carcinoma was 1.26 g while, in the group administered with the sample, it was 0.88 g whereby the inhibition rate to cancer was about 30.1% and an anticancer action was noted in the sample.

TABLE 20

| | Weight of Excised Carcinoma (grams) | Inhibiting Rate (%) |
|---|---|---|
| Control Group | | |
| | 1.23 | |
| | 1.21 | |
| | 1.34 | |
| | 1.52 | |
| | 1.74 | |
| | 1.15 | |
| | 1.09 | |
| | 0.76 | |
| | 1.26 ± 0.10 in average | 0% |
| Group Administered with the Sample | | |
| | 1.69 | |
| | 1.61 | |

TABLE 20-continued

| | Weight of Excised Carcinoma (grams) | Inhibiting Rate (%) |
|---|---|---|
| | 0.33 | |
| | 0.14 | |
| | 0.17 | |
| | 0.99 | |
| | 1.21 | |
| | 0.88 ± 0.25 in average | 30.1% |

Example 28

Murine leukemia cell line P-388 ($1 \times 10^6$ cells/ml) was incubated in vitro for six hours together with the sample (1 mg/ml) prepared in Example 27 in an RPMI 1640 medium containing 10% fetal bovine serum and, after that, 1 ml/mouse of the resulting one was intraperitoneally injected as it was to a DBA/2 mouse of five weeks age (female; body weight ca. 20 grams). (P-388:$1 \times 10^6$ cells/mouse; the sample: 50 mg/kg)

On the other hand, in the control group, P-388 incubated under the same condition was injected into the mouse together with the physiological saline solution instead of the sample.

Figure 15:
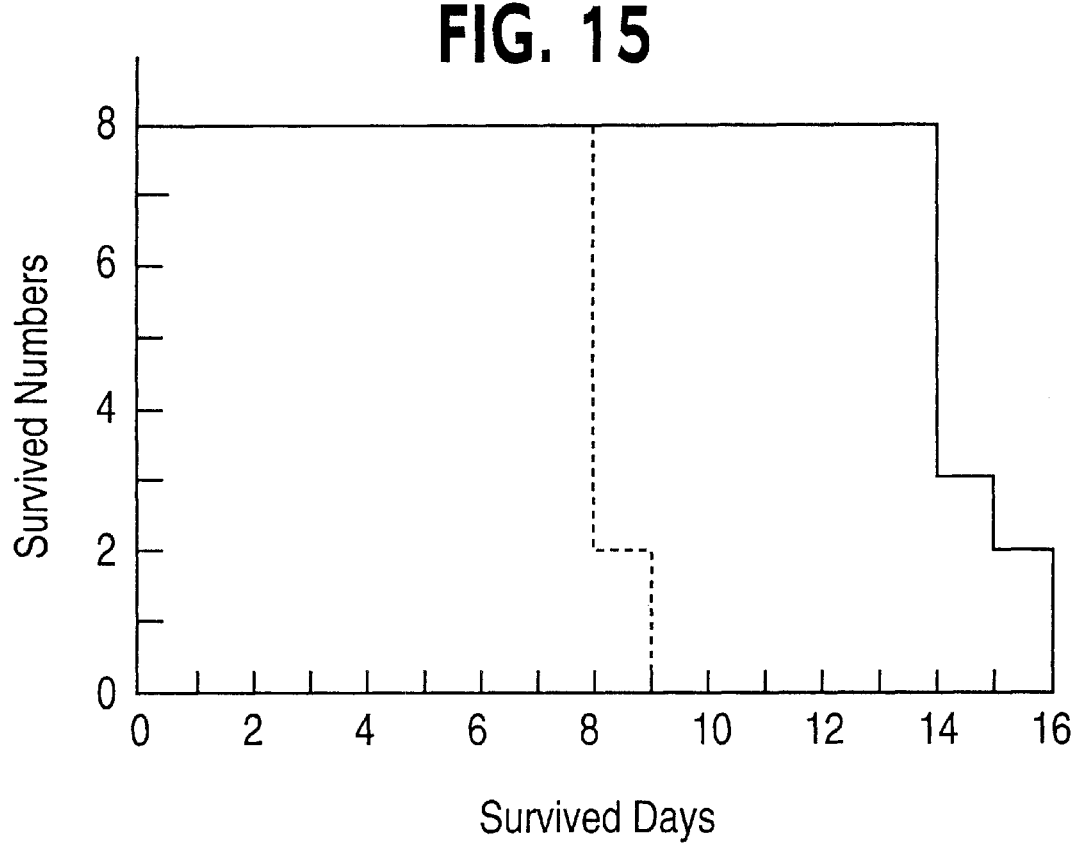
FIG. 15 shows an anticancer action of a heat-treated product of pectin to a leukemia cell line.

In the two groups (each group comprising eight mice), survived numbers, average survived days and survival rate were calculated and the results are given in FIG. 15. Thus, FIG. 15 shows an anticancer action of the sample to leukemia cells in which abscissa and ordinate are survived days and survived numbers, respectively, of the mice. In the figure, a broken line and a solid line are the control group and the group administered with the sample, respectively. Thus, in the control group, average survived days are 8.0 days while, in the group administered with the sample, average survived days are 14.6 days whereby the survival rate is 182.5% and a significant surviving effect was noted in the sample.

In the experiments which were conducted at the same time, there was no difference in terms of the survival rate of P-388 cells after an in vitro incubation for six hours between the group to which the sample was added and not added and the cell survival rate was 100% in both groups.

Example 29

Galacturonic acid or glucuronic acid was dissolved in distilled water to make the concentration 50 mg/ml and the solution was heated at 121° C. for 20 minutes and adjusted to pH7.0 with1NaOH. This was diluted with a physiological saline solution to a desired concentration and subjected to the following tests.

(1) Meth A cells ($4 \times 10^6$ cells/mouse) were subcutaneously injected to the abdominal region of a BALB/c mouse of eight weeks age (female; body weight ca. 20 grams). After that, the heat-treated galacturonic acid (100 mg/kg/day) or heat-treated glucuronic acid (100 mg/kg/day) was subcutaneously injected to the same place for consecutive ten days.

After two weeks, the carcinoma tissue formed in the abdominal region of the mouse was excised and its weight was measured. The results are given in Table 21. Thus, in the control group, the average weight of carcinoma was 1.48 g while, in the groups administered with the heat-treated galacturonic acid and with the heat-treated glucuronic acid, the average weights were 0.94 g and 0.86 g, respectively whereby the inhibition rates were 26.5% and 41.9%, respectively. Thus, significant anticancer action (p<0.05 to the control group) was noted in both groups.

TABLE 21

| | Numbers of Mice | Carcinoma Wt (g) (average ± SD) | Inhibition Rate |
|---|---|---|---|
| Control Group | 8 | 1.48 ± 0.54 | — |
| Group Administered with Heat-Treated Galacturonic Acid | 6 | 0.94 ± 0.25 | 26.5% |
| Heat-Treated Glucuronic acid | 7 | 0.86 ± 0.31 | 41.9% |

(2) Sarcoma-180 ($5.5 \times 10^6$ cells/mouse) was subcutaneously injected into the abdominal region of 16 female ICR mice (body weight: ca. 26 grams) of six weeks age and divided into eight mice for control group and eight mice for group administered with heat-treated glucuronic acid.

The group administered with heat-treated glucuronic acid was freely fed with the heat-treated glucuronic acid from a water-supplying bottle where the acid was diluted with tap water so as to make the dose of the heat-treated glucuronic acid about 1 g/kg/day. In the control group, tap water was given by the same manner. With respect to a feed, both groups were allowed to take it freely during the term of the experiment.

The survived numbers after 35 days from the subcutaneous injection of Sarcoma-180 were two out of eight in the control group while they were eight out of eight in the group administered with the heat-treated glucuronic acid. Thus, a remarkable survival effect by oral administration of heat-treated glucuronic acid was noted.

Example 30

Murine leukemia cell line P-388 ($1 \times 10^6$ cells/ml) was incubated for six hours in vitro in an RPMI 1640 medium containing 10% fetal bovine serum together with a heat-treated galacturonic acid (1 mg/ml) or a heat-treated glucuronic acid (1 mg/ml) prepared in Example 29 and then 1 ml of it was intraperitoneally injected to DBA/2 mouse (female; body weight ca. 20 grams) (P-388: $1 \times 10^6$ cells/mouse; heat-treated acid: 50 mg/kg). To the control group were injected P-388 cells ($1 \times 10^6$ cells/mouse) incubated under the same condition together with a physiological saline solution. Incidentally, in the experiment conducted at the same time, there was no difference in terms of the survival rate of the P-388 cells after an in vitro incubation for six hours between the group administered with a heat-treated acid and that with a physiological saline solution and the survival rates were 100% in both groups.

Each eight mice were used for each group and the average survived days and survival rate were calculated from the survived numbers of the mice.

The result are shown in FIG. 16. Thus, FIG. 16 shows the relationship between the days after transplantation of the P-388 cells and the survived numbers of mice in each of the groups where an ordinate shows survived numbers of mice while an abscissa shows the survived days of mice. In the figure, a solid line, a broken line and a two-dot chain line show the control group, the group administered with the heat-treated galacturonic acid and the group administered with the heat-treated glucuronic acid, respectively.

As calculated from the results of FIG. 16, the average survived days was 11.4 days in the control group while, in the group administered with the heat-treated galacturonic acid (50 mg/kg), the average survived days were 23.5 days or more and the survival rate was 206.1% or more on 24th days after the transplantation of the cells and, in the group administered with the heat-treated glucuronic acid (50 mg/kg), the average survived days were 16.8 days and the survival rate as 147.3% whereby significant surviving effect was noted as compared with the control group.

Example 31

D-Glucuronic acid (10 g) (G5269 manufactured by Sigma) was dissolved in one liter of water, heated at 121° C. for four hours and neutralized to pH 7.0 with NaOH.

The heat-treated product (500, 5 or 0.05 micrograms/ml) was added to an RPMI 1640 medium containing 10% of fetal bovine serum containing $1 \times 10^5$/ml of HL-60 cells (ATCC CCL-240) and was incubated at 37° C. for three days in the presence of 5% carbon dioxide gas. Then a part of the incubated cells were smeared on a slide glass, subjected to a Wright-Giemsa stain mentioned in page 191 of "Tissue Culture Techniques" (edited by Japan Tissue Culture Society, published by Asakura Shoten, 1982) and the degree of differentiation was observed under an optical microscope. The result was that depending upon the concentration of the heat-treated glucuronic acid which was added thereto, the cancer cells were differentiated to monocytes or to macrophage-like cells and the ratio of the mature bone marrow cells in the incubated cells was increased. The results are shown in FIG. 17. Thus, FIG. 17 shows the relationship between the incubating time and ratio of the mature bone marrow cells in the incubated cells where the abscissa and the ordinate shows the incubated time (days) and the ratio (%) of the mature bone marrow in the incubated cells, respectively. In FIG. 17, open square shows the group where no sample was added (control); open rhombus shows the group where 500 micrograms/ml of heat-treated glucuronic acid was added; open circle shows the group where 5 micrograms/ml of heat-treated glucuronic acid was added; and open triangle shows the group where 0.05 microgram/ml of heat-treated glucuronic acid was added.

Example 32

Antiulcer Action of Heat-Treated Glucuronic Acid.

D-Glucuronic acid (G5269 manufactured by Sigma) was dissolved in distilled water to make the concentration 10 mg/ml, heated at 121° C. for four hours, adjusted to pH 7.0 with1 NaOH and concentrated to 200 mg/ml by means of a freeze-drying to prepare a heat-treated glucuronic acid concentrate. This was subjected to the following experiments.

Wistar strain rats (body weight: 220–275 grams) were fasted for 24 hours and, since three hours before the initiation of the experiment, no water was given to them.

One ml of 99.5% ethanol was orally given to a rat and, one hour thereafter, stomach was excised under anesthetization with ether. Pylorus and cardia of the excised stomach were ligated, a 1% formalin solution was infused and the stomach was immersed in said solution for ten minutes. Then the stomach was cut out along a greater curvature and the length (mm) of the tumor generated in the stomach gland region was measured.

In the group administered with heat-treated glucuronic acid, the above-mentioned heat-treated glucuronic acid concentrate was orally given at the rate of 1 g/kg before 30 minutes of administration of ethanol. Distilled water was given to the control group by the same manner.

Length of the ulcer after one hour from the administration of ethanol was 78.2±28.5 mm (average±standard deviation)

in the control group (N=6) while, in the group (N=3) administered with the heat-treated glucuronic acid, no ulcer was noted at all whereby a remarkable antiulcerative action was noted.

Example 33

Injection

The sample prepared by evaporation of the ethanol-treated supernatant fraction as mentioned in Example 8 was dissolved in distilled water for injection to prepare a 1% solution. This solution was packed in vials for freeze-drying in an amount of 10 mg/vial based upon the above-mentioned sample from the supernatant fraction and then freeze-dried. A physiological saline solution (2 ml) was separately attached thereto as a solvent for dissolution.

Example 34

Injection

Galacturonic acid was dissolved in distilled water for injection to make the concentration 10 mg/ml, heated at 121° C. for 20 minutes, cooled and neutralized to prepare a neutral solution of the heat-treated acid. This solution was packed in vials for freeze-drying in an amount of 50 mg based upon the dried heat-treated acid and then freeze-dried. A physiological saline solution (2 ml) was separately attached thereto as a solvent for dissolution.

Example 35

Tablets

Tablets were prepared in accordance with the following formulation.

| | |
|---|---|
| Heat-treated pectic acid | 10 mg |
| Corn starch | 65 mg |
| Carboxymethylcellulose | 20 mg |
| Polyvinylpyrrolidone | 3 mg |
| Magnesium stearate | 2 mg |
| Total | 100 mg per tablet |

Pectin was heated by the method mentioned in Example 7, neutralized, freeze-dried and the resulting freeze-dried product was used as the heat-treated pectin.

Example 36

Green tea was prepared according to a conventional method using 10 g of green tea leaves, 0.2 g of vitamin C and 1,000 ml of deionized water. The heat-treated pectin solution I mentioned in Example 16 was added in an amount of 50 mg (based upon a solid) to 100 ml of the product whereupon the product (1) of the present invention was prepared. The control was that to which nothing was added. An organoleptic evaluation (by a five-point method where point 5 was good and point 1 was bad) was conducted by 20 panelists and the averages of the results are shown in Table 22.

TABLE 22.

| Organoleptic Evaluation | | |
|---|---|---|
| | Product (1) | Control |
| Breadth of Taste | 4.1 | 3.2 |
| Balance of Taste | 3.8 | 3.4 |
| Total Taste | 4.1 | 3.3 |

From Table 22, the evaluation was that, as compared with the control, the product (1) of the present invention had wider and broader taste and well-balanced taste whereupon flavor and taste of the tea were improved and an effect of "a hidden flavor" was achieved.

Example 37

An alcoholic beverage was prepared by a conventional method in accordance with a compounding as shown in Table 23.

TABLE 23

| Table of Compounding | |
|---|---|
| Frozen concentrated juice of Citrus unshiu (45 Brix degree) | 110 g |
| Granulated sugar | 80 g |
| Citric acid | 2 g |
| Sodium citrate | 0.5 g |
| Orange essence | 2 g |
| 5% (v/v) Aqueous solution of alcohol | balance |
| Total | 1,000 ml |

Note:
The beverage prepared as such was cooled at 5° C. and then carbonic acid was made contained therein by means of a soda siphon.

The heat-treated pectin solution I mentioned in Example 16 was added in an amount of 45 mg (based upon a solid) to 100 ml of the product whereupon the product (2) of the present invention was prepared. The control was that to which nothing was added. An organoleptic evaluation was conducted by the same manner as in Example 36. The results are given in Table 24.

TABLE 24

| Organoleptic Evaluation | | |
|---|---|---|
| | Product (2) | Control |
| Breadth of Taste | 3.9 | 3.3 |
| Balance of Taste | 4.0 | 2.7 |
| Total Taste | 3.9 | 3.0 |

As shown in Table 24, it was noted that, as compared with the control, the product (2) of the present invention had wider and broader taste. Particularly in this product (2), the acidic taste became milder and the finish was that the flavor and taste of the large mandarin (Citrus unshiu) were enhanced.

Example 38

The product (3) of the present invention was prepared from a conventionally-prepared sake (Japanese rice wine) by adding the heat-treated pectin solution II of Example 9 in an amount of 35 mg (as a solid) per 100 ml of the final product. A product to which no heat-treated pectin solution was added was used as a control.

The organoleptic evaluation was conducted by the same manner as in Example 36. Aroma and feel on the tongue were added to the evaluating items and the results are given in Table 25.

TABLE 25

Organoleptic Evaluation

|  | Product (3) | Control |
|---|---|---|
| Breadth of Taste | 3.8 | 3.0 |
| Balance of Taste | 3.4 | 2.9 |
| Aroma | 2.9 | 2.9 |
| Feel on the Tongue |  |  |
| Mildness | 3.8 | 2.6 |
| Smoothness | 4.0 | 2.9 |
| Total Taste | 3.6 | 2.8 |

As shown in Table 25, it was noted that, as compared with the control, the product (3) of the present invention had wider and broader taste and improved feel on the tongue and accordingly that the taste and the feel upon drinking as table luxuries were improved.

Example 39

The product (4) (mirin—a sweet sake) and the product (5) (fermented seasoning) of the present invention were prepared from the conventionally-prepared mirin and fermented seasoning by adding the heat-treated pectin solution I of Example 16 in an amount of 40 mg (as a solid) per 100 ml of each of the final products. Products to which no heat-treated pectin solution were added was used as controls.

The organoleptic evaluation was conducted by the same manner as in Example 36. The results are given in Table 26.

TABLE 26

Organoleptic Evaluation

|  | Mirin | | Fermented Seasoning | |
|---|---|---|---|---|
|  | Product (4) | Control | Product (5) | Control |
| Breadth of Taste | 3.8 | 3.0 | 2.9 | 2.4 |
| Balance of Taste | 3.5 | 3.0 | 2.7 | 2.1 |
| Total Taste | 3.6 | 3.1 | 2.8 | 2.2 |

As shown in Table 26, it was noted that, as compared with each of the controls, the products (4) and (5) of the present invention showed improvements in the balance and the breadth of the taste and accordingly that seasonings having a deep taste can be prepared.

Example 40

Fish powder (4.7 kg), 0.8 kg of sea algae, 2.5 kg of sesame, 1.0 kg of salt and 0.5 kg of sodium glutamate were mixed and the mixture was granulated by a conventional method to prepare furikake (seasoned fish flour).

A product (6) of the present invention was prepared by adding 1,000 mg (as a solid) of the heat-treated pectin solution II of Example 9 per 100 g of the product. No heat-treated pectin solution was added was used as a control. Those were sprinkled on boiled rice and the organoleptic evaluation in terms of feel on eating was conducted by the same manner as in Example 36.

The result was that, as compared with the control, the product (6) of the present invention well fitted the boiled rice in the mouth, had a well-balanced taste and a mild finish and, as a whole, exhibited an improved quality as a furikake.

Example 41

A beverage was prepared using the heat-treated vegetable and fruits. The compounding is shown in Table 27.

TABLE 27

| Carrot (rhizome) | 200 g |
|---|---|
| Pineapple (fruit) | 500 g |
| Banana (fruit) | 500 g |
| Granulated sugar | 76 g |
| Anhydrous citric acid | 2 g |
| Water | balance |
| Total | 2000 g |

Each of carrot, pineapple and banana in the compounding as shown in Table 27 was well stirred and disintegrated using a commercially available mixer to prepare puree of each of them. Then each of those purees was heated at 121° C. for four hours in a tightly closed state and, after that, they were mixed in accordance with the above table to prepare a beverage of the present invention.

On the other hand, each of those vegetable/fruits were not heated but their disintegrated product was just mixed according to the above table to prepare a control beverage. Organoleptic evaluation of the product of the present invention and the control was conducted by the same manner as in Example 36. The results are shown in Table 28.

TABLE 28

Organoleptic Evaluation (Average Values)

|  | Product of the Invention | Control |
|---|---|---|
| Aroma | 3.5 | 3.0 |
| Taste | 4.0 | 2.6 |
| Texture | 4.3 | 3.2 |
| Total Evaluation | 4.0 | 2.8 |
| Comments | Mild; well-mixed taste; united feel of aroma; mild feel on the tongue | No mild feel; separated tastes; aroma was not well-balanced; and a bit rough on the tongue |

From Table 28, it was noted that, as compared with the control, the product of the present invention had a mild feel, showed a well-mixed taste, had a united feel of aroma and exhibited a mild feel on the tongue whereby an appreciable beverage was prepared.

The pharmaceutical agent of the present invention can be used as a therapeutic agent for infectious diseases, lowered or risen immune function, cancerous diseases, viral diseases, ulcer, peridontal diseases, and the like. Further, an apoptosis-inducing method of the present invention is useful in studying the relation between apoptosis and defensive mechanism of living body, immune function and cancerous and viral diseases and also in developing the inhibitors for induction of apoptosis. Particularly, the saccharide compounds of the present invention in edible products have a long history as food and the heat-treated product of the present invention prepared from them is of a very high safety when given orally. In addition, it is a matter of course that the food or beverage containing the heat-treated product of the present invention and the food, beverage or antiseptic agent for food or beverage prepared by adding and/or diluting the heat-treated product of the present invention are of high safety and, due to their apoptosis-inducing action, anticancer action, antiangiogenic action, antiviral action, antiulcer action, and the like, they are very useful for prevention and therapy of gastrointestinal cancer, viral disease such as cold by influenza virus, ulcer, and the like, and also for improvement of hepatic function.

As mentioned hereinabove, the heat-treated product of the present invention can be easily manufactured in a low cost and, when it is used as an additive to food or beverage, it can give various physiological functions, antibacterial action, apoptosis-inducing action, anticancer action, antiviral action, and the like, due to its various physiological functions whereby the heat-treated product of the present invention is quite useful as an additive to food or beverage, particularly as an antiseptic agent for food and beverage.

What is claimed is:

1. A method of inducing apoptosis comprising administering, as an effective component, a product obtained by heating a substance selected from the group consisting of (a) an uronic acid or uronic acid derivative, (b) a saccharide compound comprising an uronic acid or uronic acid derivative, (c) a substance comprising a saccharide compound comprising an uronic acid or uronic acid derivative and (d) a mixture thereof.

2. The method according to claim 1, wherein the uronic acid is galacturonic acid, glucuronic acid, guluronic acid, mannuronic acid or iduronic acid.

3. The method according to claim 1, wherein the uronic acid derivative is selected from the group consisting of uronic acid lactone, uronic acid ester, uronic acid amide and salts thereof.

4. The method according to claim 1, wherein the saccharide compound is selected from the group consisting of pectin, pectic acid, alginic acid, hyaluronic acid, heparin, fucoidan chondroitin sulfate, chondroitin, dermatan sulfate and decomposed products thereof.

5. The method according to any one of claims 1 and 2–4, wherein the substance is heated at 60–350° C. for several seconds to several days.

6. The method according to any one of claims 1 and 2–4, wherein the substance is heated under acidic to neutral conditions.

7. The method according to claim 1, wherein the product is further obtained by molecular weight fractionation of the substance after heating.

8. A method of inducing apoptosis comprising administering, as an effective component, a product obtained by heating a substance selected from the group consisting of (a) an uronic acid or uronic acid derivative, (b) a saccharide compound comprising an uronic acid or uronic acid derivative, (c) a substance comprising a saccharide compound comprising an uronic acid or uronic acid derivative and (d) a mixture thereof, and molecular weight fractionating the heated substance to obtain the product.

* * * * *